US010056639B2

(12) United States Patent
Esswein et al.

(10) Patent No.: US 10,056,639 B2
(45) Date of Patent: *Aug. 21, 2018

(54) AQUEOUS REDOX FLOW BATTERIES FEATURING IMPROVED CELL DESIGN CHARACTERISTICS

(71) Applicant: LOCKHEED MARTIN ADVANCED ENERGY STORAGE, LLC, Bethesda, MD (US)

(72) Inventors: Arthur J. Esswein, San Francisco, CA (US); Steven Y. Reece, Cambridge, MA (US); Evan R. King, Quincy, MA (US); John Goeltz, Carmel, CA (US); Desiree D. Amadeo, Lunenburg, MA (US)

(73) Assignee: Lockheed Martin Energy, LLC, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/162,470

(22) Filed: May 23, 2016

(65) Prior Publication Data

US 2016/0268623 A1 Sep. 15, 2016

Related U.S. Application Data

(63) Continuation of application No. 14/164,839, filed on Jan. 27, 2014, now Pat. No. 9,382,274, which is a continuation-in-part of application No. 13/796,004, filed on Mar. 12, 2013, now Pat. No. 8,691,413, said application No. 14/164,839 is a continuation-in-part of application No. 13/795,878, filed on Mar. 12, 2013, now Pat. No. 8,753,761.

(60) Provisional application No. 61/739,538, filed on Dec. 19, 2012, provisional application No. 61/739,140, filed on Dec. 19, 2012, provisional application No. 61/738,546, filed on Dec. 18, 2012, provisional application No. 61/683,260, filed on Aug. 15, 2012, provisional application No. 61/676,473, filed on Jul. 27, 2012, provisional application No. 61/739,145, filed on Dec. 19, 2012.

(51) Int. Cl.
*H01M 8/18* (2006.01)
*H01M 8/20* (2006.01)
*C07F 7/28* (2006.01)
*H01M 4/90* (2006.01)

(52) U.S. Cl.
CPC .............. *H01M 8/188* (2013.01); *C07F 7/28* (2013.01); *H01M 4/9008* (2013.01); *H01M 8/20* (2013.01); *Y02E 60/528* (2013.01)

(58) Field of Classification Search
CPC ........... C07F 7/28; H01M 8/188; H01M 8/20; H01M 4/9008
See application file for complete search history.

(56) References Cited

U.S. PATENT DOCUMENTS

| | | |
|---|---|---|
| 1,279,295 A | 9/1918 | Downs |
| 2,353,782 A | 7/1944 | Neumark |
| 2,415,792 A | 2/1947 | Gravell |
| 3,294,588 A | 12/1966 | Morton |
| 3,425,796 A | 2/1969 | Bauer |
| 3,428,654 A | 2/1969 | Rubinfeld |
| 3,573,984 A | 4/1971 | Shah |
| 3,707,449 A | 12/1972 | Reinhardt et al. |
| 3,772,379 A | 11/1973 | Woodgate |
| 3,876,435 A | 4/1975 | Dollman |
| 3,916,004 A | 10/1975 | Okada et al. |
| 3,919,000 A | 11/1975 | Yarrington |
| 3,920,756 A | 11/1975 | Tahara et al. |
| 3,929,506 A | 12/1975 | Leddy et al. |
| 3,985,517 A | 10/1976 | Johnson |
| 3,985,585 A | 10/1976 | Tuttle et al. |
| 4,046,861 A | 9/1977 | Reinhardt et al. |
| 4,064,324 A | 12/1977 | Eustace |
| 4,069,371 A | 1/1978 | Zito |
| 4,126,529 A | 11/1978 | DeBerry |
| 4,180,623 A | 12/1979 | Adams |
| 4,202,799 A * | 5/1980 | Yoshimura ............ C07D 213/20 252/500 |
| 4,233,144 A | 11/1980 | Pace et al. |
| 4,362,791 A | 12/1982 | Kaneko et al. |
| 4,378,995 A | 4/1983 | Gratzfeld et al. |
| 4,410,606 A | 10/1983 | Loutfy et al. |
| 4,436,711 A | 3/1984 | Olson |
| 4,436,712 A | 3/1984 | Olson |
| 4,436,713 A | 3/1984 | Olson |
| 4,436,714 A | 3/1984 | Olson |
| 4,443,423 A | 4/1984 | Olson |
| 4,443,424 A | 4/1984 | Olson |
| 4,468,441 A | 8/1984 | D'Agostino et al. |
| 4,485,154 A | 11/1984 | Remick et al. |
| 4,520,083 A | 5/1985 | Prater et al. |
| 4,563,403 A | 1/1986 | Julian |
| 4,592,973 A | 6/1986 | Pemsler et al. |
| 4,617,244 A | 10/1986 | Greene |
| 4,680,308 A | 7/1987 | Schwartz et al. |

(Continued)

FOREIGN PATENT DOCUMENTS

| | | |
|---|---|---|
| CN | 1284208 A | 2/2001 |
| CN | 101877412 A | 11/2010 |

(Continued)

OTHER PUBLICATIONS

Borgias, "Synthetic, structural, and physical studies of titanium complexes of catechol and 3,5-di-tert-butylcatechol," Inorg. Chem., Apr. 1984, 23(8), 1009-1016.

(Continued)

*Primary Examiner* — Anca Eoff
(74) *Attorney, Agent, or Firm* — Baker & Hostetler LLP

(57) ABSTRACT

Provided are compositions having the formula $M_nTi(L1)(L2)(L3)$ wherein L1 is a catecholate, and L2 and L3 are each independently selected from catecholates, ascorbate, citrate, glycolates, a polyol, gluconate, glycinate, hydroxyalkanoates, acetate, formate, benzoates, malate, maleate, phthalates, sarcosinate, salicylate, oxalate, a urea, polyamine, aminophenolates, acetylacetone or lactate; each M is independently Na, Li, or K; n is 0 or an integer from 1-6. Also provided are energy storage systems.

12 Claims, 10 Drawing Sheets

(56) References Cited

U.S. PATENT DOCUMENTS

| | | |
|---|---|---|
| 4,818,646 A | 4/1989 | Takakubo et al. |
| 4,880,758 A | 11/1989 | Heistand, II et al. |
| 4,952,289 A | 8/1990 | Ciccone et al. |
| 4,959,135 A | 9/1990 | Zenner et al. |
| 4,973,720 A | 11/1990 | Saito et al. |
| 5,084,533 A | 1/1992 | Shah et al. |
| 5,122,461 A | 6/1992 | Hsiung et al. |
| 5,264,097 A | 11/1993 | Vaughan |
| 5,302,481 A | 4/1994 | Ong |
| 5,318,865 A | 6/1994 | Kaneko et al. |
| 5,433,934 A | 7/1995 | Chang et al. |
| 5,472,807 A | 12/1995 | Licht et al. |
| 5,643,670 A | 7/1997 | Chung |
| 5,679,239 A | 10/1997 | Blum et al. |
| 5,759,711 A | 6/1998 | Miyabayashi et al. |
| 5,785,841 A | 7/1998 | Tseng |
| 5,876,581 A | 3/1999 | Itaya et al. |
| 5,910,366 A | 6/1999 | Chowdhury et al. |
| 6,001,326 A | 12/1999 | Kim et al. |
| 6,030,517 A | 2/2000 | Lincot et al. |
| 6,054,230 A | 4/2000 | Kato |
| 6,461,772 B1 | 10/2002 | Miyake et al. |
| 6,475,661 B1 | 11/2002 | Pellegri et al. |
| 6,485,868 B1 | 11/2002 | Tsujioka et al. |
| 6,555,989 B1 | 4/2003 | Pearson |
| 6,585,951 B1 | 7/2003 | Hong et al. |
| 6,624,328 B1 | 9/2003 | Guerra |
| 7,046,418 B2 | 5/2006 | Lin et al. |
| 7,193,764 B2 | 3/2007 | Lin et al. |
| 7,223,833 B1 | 5/2007 | Nielsen et al. |
| 7,252,905 B2 | 8/2007 | Clarke et al. |
| 7,265,162 B2 | 9/2007 | Yandrasits et al. |
| 7,348,088 B2 | 3/2008 | Hamrock et al. |
| 7,463,917 B2 | 12/2008 | Martinez |
| 7,508,568 B2 | 3/2009 | Lin et al. |
| 7,550,231 B2 | 6/2009 | Stauffer |
| 7,557,164 B2 | 7/2009 | Felix et al. |
| 7,625,663 B2 | 12/2009 | Clarke et al. |
| 7,645,540 B2 | 1/2010 | Boone et al. |
| 7,678,728 B2 | 3/2010 | Olson et al. |
| 7,745,056 B2 | 6/2010 | Lee et al. |
| 7,767,777 B2 | 8/2010 | Buesing et al. |
| 7,927,731 B2 | 4/2011 | Sahu |
| 7,931,981 B2 | 4/2011 | Boone et al. |
| 7,935,366 B2 | 5/2011 | Pahuja et al. |
| 7,998,335 B2 | 8/2011 | Feeney et al. |
| 8,129,554 B2 | 3/2012 | Schwaiger |
| 8,187,441 B2 | 5/2012 | Evans et al. |
| 8,445,118 B2 | 5/2013 | Cordonier et al. |
| 8,492,581 B2 | 7/2013 | Frost et al. |
| 8,691,413 B2 | 4/2014 | Esswein et al. |
| 8,753,761 B2 | 6/2014 | Esswein et al. |
| 9,300,000 B2 | 3/2016 | Jansen et al. |
| 9,382,274 B2 | 7/2016 | Esswein et al. |
| 9,409,842 B1 | 8/2016 | Fu et al. |
| 2002/0177042 A1 | 11/2002 | Amendola |
| 2003/0068561 A1 | 4/2003 | Okahara et al. |
| 2003/0143456 A1 | 7/2003 | Kazacos et al. |
| 2003/0228394 A1 | 12/2003 | Abdel-Monem et al. |
| 2004/0096746 A1 | 5/2004 | Wietelmann et al. |
| 2005/0098437 A1 | 5/2005 | Shiepe |
| 2005/0244707 A1 | 11/2005 | Skyllas-Kazacos et al. |
| 2006/0047094 A1 | 3/2006 | Cherkasov et al. |
| 2007/0275291 A1 | 11/2007 | Gu et al. |
| 2008/0274385 A1 | 11/2008 | Creeth |
| 2008/0292964 A1 | 11/2008 | Kazacos et al. |
| 2009/0110998 A1 | 4/2009 | Miyachi et al. |
| 2009/0130525 A1 | 5/2009 | Miyachi et al. |
| 2009/0208807 A1 | 8/2009 | Miyachi et al. |
| 2009/0308752 A1 | 12/2009 | Evans et al. |
| 2010/0003586 A1 | 1/2010 | Sahu |
| 2010/0059388 A1 | 3/2010 | Clarke et al. |
| 2010/0086823 A1 | 4/2010 | Koshino et al. |
| 2010/0086983 A1 | 4/2010 | Gellett et al. |
| 2010/0239946 A1 | 9/2010 | Miyachi et al. |
| 2011/0014532 A1 | 1/2011 | Knuckey et al. |
| 2011/0136016 A1 | 6/2011 | Huang et al. |
| 2011/0189549 A1 | 8/2011 | Sun et al. |
| 2011/0195283 A1 | 8/2011 | Sun et al. |
| 2011/0200890 A1 | 8/2011 | Kocherginsky |
| 2011/0223450 A1 | 9/2011 | Horne et al. |
| 2011/0244277 A1 | 10/2011 | Gordon, II et al. |
| 2011/0244367 A1 | 10/2011 | Watahiki et al. |
| 2012/0052347 A1 | 3/2012 | Wilson et al. |
| 2012/0077095 A1 | 3/2012 | Roumi et al. |
| 2012/0107661 A1 | 5/2012 | Lee et al. |
| 2012/0135278 A1 | 5/2012 | Yoshie et al. |
| 2012/0171541 A1 | 7/2012 | Park et al. |
| 2012/0183868 A1 | 7/2012 | Toussaint et al. |
| 2012/0196188 A1 | 8/2012 | Zhang et al. |
| 2012/0202099 A1 | 8/2012 | Perry et al. |
| 2012/0208061 A1 | 8/2012 | Sahu et al. |
| 2012/0244406 A1 | 9/2012 | Xia et al. |
| 2012/0263990 A1 | 10/2012 | Kim |
| 2013/0004819 A1 | 1/2013 | Mun et al. |
| 2013/0157087 A1 | 6/2013 | Pandy et al. |
| 2013/0252062 A1 | 9/2013 | Wilkins et al. |
| 2013/0252137 A1 | 9/2013 | Zhang et al. |
| 2014/0028260 A1 | 1/2014 | Goeltz et al. |
| 2014/0028261 A1 | 1/2014 | Esswein et al. |
| 2014/0030572 A1 | 1/2014 | Esswein et al. |
| 2014/0030573 A1 | 1/2014 | Esswein et al. |
| 2014/0030631 A1 | 1/2014 | Esswein et al. |
| 2014/0051003 A1 | 2/2014 | Esswein et al. |
| 2014/0080035 A1 | 3/2014 | Esswein et al. |
| 2014/0138576 A1 | 5/2014 | Esswein et al. |
| 2014/0178735 A1 | 6/2014 | Wang et al. |
| 2014/0193687 A1 | 7/2014 | Park et al. |
| 2014/0239906 A1 | 8/2014 | Anderson et al. |
| 2014/0274936 A1 | 9/2014 | Piccariello et al. |
| 2014/0349177 A1 | 11/2014 | Chung et al. |
| 2014/0377666 A1 | 12/2014 | Kodama et al. |
| 2015/0236543 A1 | 8/2015 | Brushett et al. |
| 2015/0372333 A1 | 12/2015 | Odom et al. |
| 2016/0066578 A1 | 3/2016 | Ala'Aldeen et al. |
| 2016/0149251 A1 | 5/2016 | Reece |
| 2016/0208165 A1 | 7/2016 | Li et al. |
| 2016/0264603 A1 | 9/2016 | Esswein et al. |
| 2016/0272659 A1 | 9/2016 | King et al. |
| 2016/0276693 A1 | 9/2016 | Goeltz et al. |
| 2016/0276694 A1 | 9/2016 | Goeltz et al. |
| 2016/0276695 A1 | 9/2016 | Esswein et al. |
| 2017/0253620 A1 | 9/2017 | Humbarger et al. |
| 2017/0256811 A1 | 9/2017 | Humbarger et al. |
| 2017/0271704 A1 | 9/2017 | Morris-Cohen |

FOREIGN PATENT DOCUMENTS

| | | |
|---|---|---|
| EP | 0814527 A2 | 12/1997 |
| EP | 1290068 A2 | 3/2003 |
| EP | 1411576 A1 | 4/2004 |
| EP | 1901379 A1 | 3/2008 |
| EP | 2235781 A1 | 10/2010 |
| EP | 2463950 A1 | 6/2012 |
| FR | 1533662 A | 7/1968 |
| GB | 1354886 A | 6/1974 |
| JP | S 57009073 A | 1/1982 |
| WO | WO-95/12219 A1 | 5/1995 |
| WO | WO-1997/017354 A1 | 5/1997 |
| WO | WO-2004/095602 A2 | 11/2004 |
| WO | WO-2006/135958 A1 | 12/2006 |
| WO | WO-2007/044852 A2 | 4/2007 |
| WO | WO-2007/101284 A1 | 9/2007 |
| WO | WO-2011/075135 A1 | 6/2011 |
| WO | WO-2011/098781 A1 | 8/2011 |
| WO | WO-2011/149624 A1 | 12/2011 |
| WO | WO-2012/075810 A1 | 6/2012 |
| WO | WO-2013/006427 A1 | 1/2013 |

(56) References Cited

FOREIGN PATENT DOCUMENTS

WO WO-2013/048603 A1 4/2013
WO WO-2015/069439 A1 5/2015

OTHER PUBLICATIONS

Brezina, "Study of the reduction of oxygen on a carbon paste electrode in an alkaline medium," Coll. Czech. Chem. Commun., 1973, 38(10), 3024-3031.
Caulton, "Systematics and Future Projections Concerning Redox-Noninnocent Amide/Imine Ligands," Eur. J. Inorg. Chem., Jan. 2012, 2012(3), 435-443.
Cerofontain et al. "Sulfonation and sulfation on reaction of 1,2-dihydroxybenzene and its methyl ethers in concentrated aqueous sulfuric acid," Recl Trav Chim Pays-Bas, 1988, pp. 325-330, vol. 107.
Chen, "Solution Redox Couples for Electrochemical Energy Storage: I. Iron (III)-Iron (II) Complexes with O-Phenanthroline and Related Ligands," Journal of the Electrochemical Society, Jul. 1981, 128(7), 1460-1467.
Cohen, "The Association of Ferrocyanide Ions With Various Cations," J. Phys. Chem., Aug. 1957, 61(8), 1096-1100.
Davies, "Electroceramics from Source Materials via Molecular Intermediates: PbTiO3 from TiO2 via [Ti(catecholate)3]2-," J. Am. Ceram. Soc., Aug. 1990, 73(8), 2570-2572.
Dehaen et al, "A Self-Assembled Complex with a Titanium (IV) Catecholate Core as a Potential Bimodal Contrast Agent," Chem Eur J, 2012, pp. 293-302, vol. 18.
Fryda, "Wastewater Treatment With Diamond Electrodes," Diamond Materials, Electrochemical Society Proceedings, 2000, 99(32), 473-483.
Gail, "Cyano Compounds, Inorganic" in Ullmann's Encyclopedia of Industrial Chemistry, 2012, 10, 674-710.
Hollandsworth, "Zinc/Ferrocyanide Battery Development Phase IV" Lockheed Missiles and Space Company, Inc., Contractor report, Sandia Contract DE-AC04-76DP00789, May 1985, 278 pages.
Kim, "Novel catalytic effects of Mn3O4 for all vanadium redox flow batteries," Chem. Commun., Apr. 2012, 48(44), 5455-5457.
Kulesza, "Electrochemical preparation and characterization of hybrid films composed of Prussian blue type metal hexacyanoferrate and conducting polymer," Electrochimica Acta, Aug. 2001, 46(26-27), 4065-4073.
Leung, "Development of a Zinc--Cerium Redox Flow Battery", 2011, 352 pages.
Leung, "An undivided zinc--cerium redox flow battery operating at room temperature (295 K)," Electrochemistry Communications, 2011, vol. 13, pp. 770-773.
Leung, "Ce(III)/Ce(iV) in methanesulfonic acid as the positive half cell of a redox flow battery," Electrochimica Acta, 2011, vol. 56, pp. 2145-2153.
Leung, "Zinc deposition and dissolution in methanesulfonic acid onto a carbon composite electrode as the negative electrode reactions in a hybrid redox flow battery," Electrochimica Acta, 2011, vol. 56, pp. 6536-6546.
Leung, "Characterization of a zinc--cerium flow battery," Journal of Power Sources, 2011, vol. 195, pp. 5174-5185.
Modiba, "Electrochemical impedance spectroscopy study of Ce(IV) with aminopolycarboxylate ligands for redox flow batteries applications," Journal of Power Sources, May 2012, vol. 205, 1-9.
Modiba, "Electrochemical Study of cerium(IV) in the presence of ethylenediaminetetraacetic acid (EDTA) and diethylenetriaminepentaacetate (DTPA) ligands," Journal of Applied Electrochemistry, Sep. 2008, 38(9), 1293-1299.
Modiba, "Electrolytes for redox flow battery systems," Dissertation presented for the degree of Doctor of Philosophy Chemistry at the University of Stellenbosch, Department of Chemistry and Polymer Science, Mar. 2010.
Nguyen, "Flow Batteries," the Electrochemical Society Interface, Fall 2010, 19(3), 54-56.
Pharr, "Infrared Spectroelectrochemical Analysis of Adsorbed Hexacyanoferrate Species Formed during Potential Cycling in the Ferrocyanide/Ferricyanide Redox Couple," Anal. Chem., Nov. 1997, 69(22), 4673-4679.
Raymond, "Coordination isomers of biological iron transport compounds. VI. Models of the enterobactin coordination site. A crystal field effect in the structure of potassium tris( catecholato )chromate( III) and -ferrate( III) sesq u ihyd rates, K3[M( O2C6H4 )3]. 1 . 5H2O, M=chromium, iron," J. Am. Chem. Soc., Mar. 1976, 98(7), 1767-1774. cited by applicant.
Saito et al. "DPPH radical-scavenging reaction of protocatechuic acid: differnce in reactivity between acids and their esters," Helv Chim Acta, 2006, pp. 1395-1407, vol. 89.
Sever et al, "Visible absorption spectra of metal-catecholate and metal-tironate complexes," Dalton Trans., pp. 1061-1072, 2004.
SIGMA-ALDRICH Tris(hydroxymethyl)aminomethane, 2015.
Sommer, "Titanium (IV) complexes with ligands having oxygen donor atoms in aqueous solutions," Zeitschrift fur Anorganische and Aligemeine Chemie, Mar. 1963, pp. 191-197, vol. 321, issue 3-4.
Steenken, "One-electron redox potentials of phenols. Hydroxy- and aminophenols and related compounds of biological interest," J. Phys. Chem., Sep. 1982, 86(18), 3661-3667.
Torres-Gomez, "Energy Storage in Hybrid Organic-Inorganic Materials Hexacyanoferrate-Doped Polypyrrole as Cathode in Reversible Lithium Cells," J. of the Electrochemical Society, 2000, 147(7), 2513-2516.
Trant, "Solubility of Sodium Ferrocyanide and Potassium Ferrocyanide in Solutions of NaOH and KOH Mixtures at 25.degree. C," University of Rochester, the David T. Kearns Center, Xerox Undergraduate Research Fellows Program, Jul. 28, 2011, 1 page.
Vercillo, "Solubility of Sodium Ferrocyanide in Sodium Hydroxide and Potassium Ferrocyanide in Potassium Hydroxide," University of Rochester, the David T. Kearns Center, Xerox Undergraduate Research Fellows Program, Jul. 28, 2011, 1 page.
Wang, "Determination of iron, titanium, osmium, and aluminum with tiron by reversephase high performance liquid chromatography/electrochemistry," Microchem. J., Jun. 1991, 43(3), 191-197.
Weber, "Redox flow batteries: a review," Journal of Applied Electrochemistry, Oct. 2011, 41(10), 1137-1164.
Murakami et al., "The Chelating Behavior of Catechol-4-sulfonate with Iron(III) Ion," Bulletin of the Chemical Society of Japan, 1963, pp. 1408-1411; vol. 36.
Westervelt, "A Study of the Calcium Complex of the Potassium Salt of Catechol-4-Sulfonate in Aqueous, Alkalino Media," Jan. 1981, Doctoral Dissertation, retrieved from https://smartech.gatech.edu/bitstream/handle/1853/5723/westervelt-iii_hh.pdf.
Ahn et al., "A Study of Benzene 1,2,4-Trisphosphate Derivatives as Inositol 1,4,5-Trisphosphate 3-Kinase Inhibitors," Bull. Korean Chem. Soc., 2002, pp. 515-517, vol. 23., No. 3.
Bosch et al., "Novel Catalysis of Hydroquinone Autoxidation with Nitrogen Oxides," J. Org. Chem., 1994, pp. 2529-2536, 59.
Lang et al., "Studies on the Biosynthesis of Bovilactone-4,4 and Related Fungal Meroterpenoids," Eur. J. Org. Chem., 2008, pp. 3544-3551.
Lang et al., "Studies on the Structure and Biosynthesis of Tridentoquinone and Related Meroterpenoids from the Mushroom *Suillus tridentinus* (Boletales)," Eur. J. Org. Chem., 2008, pp. 816-825.
Mcomie et al. "The Thiele-Winter Acetoxylation of Quinones," Organic Reactions, 1972, pp. 199-277, 19, John Wiley and Sons, Inc., New York.
Spyroudis, "Hydroxyquinones: Synthesis and Reactivity," Molecules, 2000, pp. 1291-1330, 5.
W. Maison, et al., "Effect of Calcination Temperature on Phase Transformation and Particle size of Barium Titanate Fine Powders Synthesized by the Catecholate Process," ScienceAsia, 2001, pp. 239-243, 27.
Ali et al., "Synthesis and Processing Characteristics of $Ba_{0.65}Sr_{0.35}TiO_3$ Powders from Catecholate Precursors," J Am Ceram Soc, 1993, pp. 2321-2326, vol. 76, No. 9.

(56) References Cited

OTHER PUBLICATIONS

Devi et al., "pH-metric investigation on Mixed-Ligand Complexs of Ca(II), Mg(II) and Zn(II) with L-Dopa and 1,10 Phenantroline in Propylene glycol-Water Mixtures," RRJC, Oct.-Dec. 2012, vol. 1, Issue 1, pp. 13-22.
Xu, "Mechanics of metal-catecholate complexes: The roles of coordination state and metal types," Scientific Reports, Oct. 10, 2013, 3:2914, pp. 1-7.
Soloveichik, "Flow Batteries: Current Status and Trends," 2015, Chem. Rev., 115 (20), pp. 11533-11558.
Davies, "Electroceramics from Source Materials via Molecular Intermediates: $BaTiO_3$ from $TiO_2$ via $[Ti(catecholate)3]^{2-}$," May 1990, J. Am, Ceram. Soc., Aug. 1990, 73(5), 1429-30.
Vliet et al., "Hydroxyhydroquinone Triacetate," Organic Synthesys, 1941, Coll vol. 1, p. 317 (1941), vol. 4, p. 35 (1925) 3 pages.
International Search Report and Written Opinion dated Jan. 19, 2017 from International Application No. PCT/US16/58433.
International Search Report and Written Opinion dated Feb. 17, 2017 from International Application No. PCT/US16/65159.
Abdulghani et al., "Preparation and Characterization of Di-, Tri-, and Tetranuclear Schiff Base Complexes Derived from Diamines and 3,4-Dihydroxybenzaldehyde," Hindawi Publishing Corp, Bioinorganic Chemistry and Applications, 2013, pp. 1-14.
IUPAC Compendium of Chemical Terminology, "coordinatively unsaturated complex," 1997, http://old.iupac.org/goldbook/C01334.pdf.
Mansoor, "Mixed Metal Complexes of Copper (II), Nickel (II) and Zinc (II) Involving Dopa and Dopamine," International Journal of ChemTech Research, Jan.-Mar. 2010, vol. 2, No. 1, pp. 640-645.
International Search Report and Written Opinion from PCT/US17/14764, dated Apr. 20, 2017.
International Search Report and Written Opinion from PCT/US16/69190, dated May 3, 2017.
International Search Report and Written Opinion from PCT/US2017/022203, dated Jun. 6, 2017.
Wang et al., "Issues in Freeze Drying of Aqueous Solutions," Chinese Journal of Chemical Engineering, 2012, 20(3), pp. 551-559.
Ahluwalia et al., Intermediates for Organic Synthesis, Chapter 1, Phenols, Sections 1.21 and 1.23, (2003), I.K. International Pvt. Ltd.
Lamberth et al., "Preparation and Second-Harmonic Generation Properties of Tris(pyrocatecholato)stannate(iv) Compounds", J. Mater. Chem., 1991, 1(5), 775-780.
Mabrouck et al., "Coordination compounds of indium. Part 45. Indium (I) derivatives of aromic diols", Can. J. Chem., 1989, 67, 746-750.

\* cited by examiner

AQUEOUS REDOX FLOW BATTERIES FEATURING IMPROVED CELL DESIGN CHARACTERISTICS

CROSS-REFERENCE TO RELATED APPLICATIONS

This application is a continuation of U.S. patent application Ser. No. 14/164,839, filed on Jan. 27, 2014, which is a continuation-in-part of U.S. patent application Ser. No. 13/796,004, filed on Mar. 12, 2013 and now U.S. Pat. No. 8,691,413, and a continuation-in-part of U.S. patent application Ser. No. 13/795,878, filed on Mar. 12, 2013 and now U.S. Pat. No. 8,753,761, each of which is incorporated herein by reference in its entirety. U.S. patent application Ser. No. 13/796,004, in turn, claims the benefit of priority of U.S. Provisional Patent Application 61/739,538, filed on Dec. 19, 2012, U.S. Provisional Patent Application 61/739,140, filed on Dec. 19, 2012, U.S. Provisional Patent Application 61/738,546, filed on Dec. 18, 2012, U.S. Provisional Patent Application 61/683,260, filed on Aug. 15, 2012, and U.S. Provisional Patent Application 61/676,473, filed on Jul. 27, 2012. U.S. patent application Ser. No. 13/795,878, in turn, claims the benefit of priority of U.S. Provisional Patent Application 61/739,145, filed on Dec. 19, 2012, U.S. Provisional Patent Application 61/738,546, filed on Dec. 18, 2012, U.S. Provisional Patent Application 61/683,260, filed on Aug. 15, 2012, and U.S. Provisional Patent Application 61/676,473, filed on Jul. 27, 2012. Each of the foregoing applications is incorporated herein by reference in its entirety.

TECHNICAL FIELD

This disclosure relates to the field of energy storage systems, including electrochemical energy storage systems, batteries, and flow battery systems and methods of operating the same.

BACKGROUND

There exists a long-felt need for safe, inexpensive, easy-to-use, and reliable technologies for energy storage. Large scale energy storage enables diversification of energy supply and optimization of the energy grid, including increased penetration and utilization of renewable energies. Existing renewable-energy systems (e.g., solar- and wind-based systems) enjoy increasing prominence as energy producers explore non-fossil fuel energy sources, however storage is required to ensure a high quality energy supply when sunlight is not available and when wind does not blow.

Electrochemical energy storage systems have been proposed for large-scale energy storage. To be effective, these systems must be safe, reliable, low-cost, and highly efficient at storing and producing electrical power. Flow batteries, compared to other electrochemical energy storage devices, offer an advantage for large-scale energy storage applications owing to their unique ability to decouple the functions of power density and energy density. Flow batteries are generally comprised of negative and positive active material electrolytes, which are flowed separately across either side of a membrane or separator in an electrochemical cell. The battery is charged or discharged through electrochemical reactions of the active materials inside the electrochemical cell.

Existing flow batteries have suffered from the reliance on battery chemistries and cell designs that result in either high cell resistance or active materials crossing over the membrane and mixing. This phenomenon results in low cell and system performance (e.g. round trip energy efficiency) and poor cycle life, among others. To be effective, the flow battery chemistry and cell components must be chosen and optimized to afford low cell resistance and low active material crossover. Despite significant development effort, no flow battery technology has yet achieved this combination. Accordingly, there is a need in the art for improved flow battery chemistry and cell design characteristics.

SUMMARY

The present disclosure addresses these challenges by providing compositions that are useful, inter alia, as active materials in flow batteries. The present disclosure provides, inter alia, compositions having the formula:

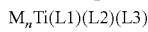
$M_nTi(L1)(L2)(L3)$ wherein:
L1 is a catecholate, and
L2 and L3 are each independently selected from catecholates, ascorbate, citrate, glycolates, a polyol, gluconate, glycinate, hydroxyalkanoates, acetate, formate, benzoates, malate, maleate, phthalates, sarcosinate, salicylate, oxalate, a urea, polyamine, aminophenolates, acetylacetone or lactate;
each M is independently Na, Li, or K;
n is 0 or an integer from 1-6; and
provided that when both L1 and L2 are a catecholate, L3 is not oxalate, urea, catecholate or acetylacetone.

In some embodiments, the catecholate comprises 1,2-dihydroxybenzene, 1,2,3-trihydroxybenzene, 1,2,4-trihydroxybenzene or a mixture thereof. Preferred embodiments include compositions having the formula

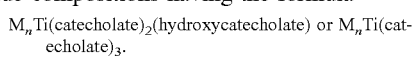
$M_nTi(catecholate)_2(hydroxycatecholate)$ or $M_nTi(catecholate)_3$.

Another aspect of the invention concerns an aqueous solution, comprising one or more compositions having the formula

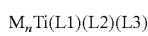
$M_nTi(L1)(L2)(L3)$ wherein:
L1 is a catecholate, and
L2 and L3 are each independently selected from catecholates, ascorbate, citrate, glycolates, a polyol, gluconate, glycinate, hydroxyalkanoates, acetate, formate, benzoates, malate, maleate, phthalates, sarcosinate, salicylate, oxalate, a urea, polyamine, aminophenolates, acetylacetone or lactate;
each M is independently Na, Li, or K;
n is 0 or an integer from 1-6.

Some solutions additionally comprise a buffer. Suitable buffers include, but are not limited to a salt of phosphate, borate, carbonate, silicate, tris(hydroxymethyl)aminomethane (tris), 4-(2-hydroxyethyl)-1-piperazineethanesulfonic acid (HEPES), piperazine-N,N'-bis(ethanesulfonic acid) (PIPES), and combinations thereof.

In some embodiments, the aqueous solution has a pH of 1-13, 2-12, 4-10 or 6-8.

In some aspects, the disclosure provides flow batteries comprising one or more of the compositions disclosed herein. In some embodiments, the composition is an active material.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings.

DETAILED DESCRIPTION OF ILLUSTRATIVE EMBODIMENTS

Figure 1:
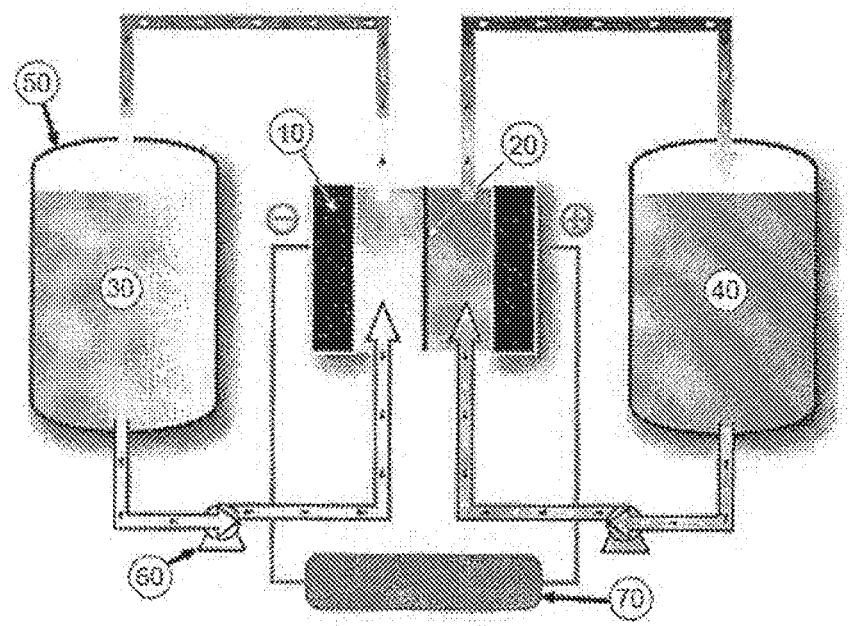
FIG. 1 depicts a schematic of an exemplary flow battery.

The present disclosure may be understood more readily by reference to the following description taken in connection with the accompanying Figures and Examples, all of which form a part of this disclosure. It is to be understood that this disclosure is not limited to the specific products, methods, conditions or parameters described and/or shown herein, and that the terminology used herein is for the purpose of describing particular embodiments by way of example only and is not intended to be limiting of any claimed disclosure. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to methods of operating a device and systems and to the devices and systems providing said methods. That is, where the disclosure describes and/or claims a method or methods for operating a flow battery, it is appreciated that these descriptions and/or claims also describe and/or claim the devices, equipment, or systems for accomplishing these methods.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

Electrochemical energy storage systems typically operate through the interconversion of electrical and chemical energy. Various embodiments of electrochemical energy storage systems include batteries, capacitors, reversible fuel cells and the like, and the present invention may comprise any one or combination of these systems.

Unlike typical battery technologies (e.g., Li-ion, Ni-metal hydride, lead-acid, etc.), where energy storage materials and membrane/current collector energy conversion elements are unitized in a single assembly, flow batteries transport (e.g., via pumping) redox active energy storage materials from storage tanks through an electrochemical stack, as in exemplary FIG. 1, which is described elsewhere herein in further detail. This design feature decouples the electrical energy storage system power (kW) from the energy storage capacity (kWh), allowing for considerable design flexibility and cost optimization.

In some embodiments, flow batteries according to the present disclosure may also be described in terms of a first chamber comprising a negative electrode contacting a first aqueous electrolyte; a second chamber comprising a positive electrode contacting a second aqueous electrolyte, and a separator disposed between the first and second electrolytes. The electrolyte chambers provide separate reservoirs within the cell, through which the first and/or second electrolyte flow so as to contact the respective electrodes and the separator. Each chamber and its associated electrode and electrolyte defines its corresponding half-cell. The separator provides several functions which include, e.g., (1) serving as a barrier to mixing of first and second electrolytes; (2) electronically insulating to reduce or prevent short circuits between the positive and negative electrodes; and (3) to provide for ion transport between the positive and negative electrolyte chambers, thereby balancing electron transport during charge and discharge cycles. The negative and positive electrodes provide a surface for electrochemical reactions during charge and discharge. During a charge or discharge cycle, electrolytes may be transported from separate storage tanks through the corresponding electrolyte chambers. In a charging cycle, electrical power is applied to the system wherein the active material contained in the second electrolyte undergoes a one-or-more electron oxidation and the active material in the first electrolyte undergoes a one-or-more electron reduction. Similarly, in a discharge cycle the second electrolyte is reduced and the first electrolyte is oxidized producing electrical power.

Various embodiments of the present invention describe flow batteries. Exemplary flow batteries suitably comprise: (a) a first aqueous electrolyte comprising a first metal ligand coordination compound; (b) a second aqueous electrolyte comprising a second metal ligand coordination compound; (c) a separator positioned between said first and second aqueous electrolytes, the separator comprising an ionomer membrane; and (d) a mobile ion, wherein the separator has a thickness of less than 100 microns and each of the first and second metal ligand coordination compound and the ionomer membrane have an associated net charge that is the same sign.

In some embodiments, at least one of the first or second metal ligand coordination compound is of the formula $M(L1)_{3-x-y}(L2)_x(L3)_y^m$, x and y are independently 0, 1, 2, or 3, such that 3-x-y is not less than zero;

m is −5, −4, −3, −2, −1, 0, +1, +2, +3, +4, or +5; and

M is Al, Cr, Fe, or Ti; and

L1, L2, and L3 are each independently ascorbate, a catecholate, a pyrogallate, lactate, gluconate, or citrate. In some cases, if x is 0, y is not 0.

Certain specific embodiments of the present invention include flow batteries, each flow battery comprising:
a first aqueous electrolyte comprising a first ionically charged redox active material;
a second aqueous electrolyte comprising a second ionically charged redox active material;
a first electrode in contact with said first aqueous electrolyte;
a second electrode in contact with said second aqueous electrolyte; and
a separator comprising an ionomer membrane disposed between said first and second aqueous electrolytes;
wherein the sign of the net ionic charge of the first, second, or both redox active materials matches that of the ionomer membrane.

The flow batteries may further comprise an external electrical circuit in electrical communication with the first and second electrodes, said circuit capable of charging or discharging the flow battery. Reference to the sign of the net ionic charge of the first, second, or both redox active materials relates to the sign of the net ionic charge in both oxidized and reduced forms of the redox active materials under the conditions of the operating flow battery. Further exemplary embodiments provide that (a) the first ionically charged redox active material has an associated net positive or negative charge and is capable of providing an oxidized or reduced form over an electric potential in a range the negative operating potential of the system, such that the resulting oxidized or reduced form of the first redox active material has the same charge sign (positive or negative) as the first redox active material, the ionomer membrane also having a net ionic charge of the same sign; and (b) the second ionically charged redox active material has an associated net positive or negative charge and is capable of providing an oxidized or reduced form over an electric potential in a range of the positive operating potential of the system, such that the resulting oxidized or reduced form of the second redox active material has the same charge sign (positive or negative sign) as the second redox active material, the ionomer membrane also having a net ionic charge of the same sign; or both (a) and (b). These matching charges of the first and/or second electrolytes and the stationary phase of the membrane, provides a selectivity such that, in individual embodiments, less than about 3%, less than about 2%, less than about 1%, less than about 0.5%, less than about 0.2%, or less than about 0.1% of the molar flux of ions passing through the membrane is attributable to the first or second ionically charged redox active material. The term "molar flux of ions" refers to the amount of ions passing through the separator membrane, balancing the charge associated with the flow of external electricity/electrons. That is, the flow battery is capable of operating or operates with the substantial exclusion of the ionically charged redox active materials by the ionomer membrane.

The present disclosure includes independent embodiments of those flow batteries wherein the sign of the net ionic charge of the first, second, or both redox active materials matches that of the ionomer membrane include those where one or more of the following features are individually or collectively present:

(A) where, during the operation of the flow battery, the first or second redox active materials comprise less than about 3% of the molar flux of ions passing through the ionomer membrane;

(B) where, the round trip current efficiency is greater than about 70%, greater than about 80%, or greater than about 90%;

(C) where the round trip current efficiency is greater than about 90%;

(D) where the sign of the net ionic charge of the first, second, or both redox active materials is the same in both oxidized and reduced forms of the redox active materials and matches that of the ionomer membrane;

(E) where the ionomer membrane has a thickness of less than about 100 µm, less than about 75 µm, less than about 50 µm, or less than about 250 µm.

(F) where the flow battery is capable of operating at a current density of greater than about 100 mA/cm$_2$ with a round trip voltage efficiency of greater than about 60%;

(G) where the energy density of the electrolytes is greater than about 10 Wh/L, greater than about 20 Wh/L, or greater than about 30 Wh/L.

In other embodiments of these flow batteries, at least one of the first or second redox active material or both first and second redox active materials comprises a metal ligand coordination compound. The term "metal ligand coordination compound" is defined below. Where the first and second redox active materials comprise first and second metal ligand coordination compounds, respectively, the first metal ligand coordination compound may be the same or different than the second metal ligand coordination compound.

In other embodiments of these flow batteries, at least one of said first or second redox active materials may be an organic compound substantially devoid of metal.

Also as described below, one or both of the first and second redox materials may exhibit substantially reversible electrochemical kinetics. Facile electrochemical kinetics, and especially reversible electrochemical kinetics are important for decreasing energy wasting electrode overpotentials in both battery charge and discharge modes. In certain embodiments, these substantially reversible electrochemical kinetics are achievable or achieved using electrodes presenting a surface of an allotrope of carbon to the respective electrolyte. One or both of the electrodes may present a surface of an allotrope of carbon to the respective electrolyte.

The aqueous electrolytes of these flow batteries may independently have a pH in a range of about 1 to about 13 pH units. In other independent embodiments, the pH of each of the first or second aqueous electrolytes or the pH of both the first and second aqueous electrolytes each exhibits a pH in a range of about 7 to about 13, about 8 to about 13, about 9 to about 13, about 10 to about 13, about 10 to about 12, or about 11. In other independent embodiments, the pH of the first aqueous electrolyte is within about 2 pH units, about 1 pH unit, or about 0.5 pH units of the pH of the second aqueous electrolyte. Additional embodied ranges for pH are provided below.

In specific embodiments, both the first and second ionically charged redox active materials and their respective oxidized or reduced forms are negatively charged, and the ion selective membrane having a stationary phase that also has a net negative charge, so as to be selectively permeable to cations to the substantial exclusion of the negatively charged redox active materials. The first and second redox active materials and their respective oxidized or reduced forms may independently exhibit charges in a range of −2 to −5. The term "substantial exclusion" refers to the ability of the membrane to limit the molar flux of ions passing through the membrane attributable to the first or second ionically charged redox active material to less than about 3% of the total ion flux during the operation of the flow battery. In related independent embodiments, the flux of ions attributable to the first or second ionically charged redox active material is less than about 5%, less than about 2%, less than about 1%, less than about 0.5%, less than about 0.2%, or less than about 0.1% of the total ion flux during the operation of the flow battery.

In other embodiments, both the first and second ionically charged redox active materials and their respective oxidized or reduced forms are positively charged, the ion selective membrane having a stationary phase that also has a net positive charge, so as to be selectively permeable to anions to the substantial exclusion of the positively charged redox active materials. The first and second redox active materials and their respective oxidized or reduced forms may independently exhibit charges in a range of +2 to +5 over the respective potential ranges. The term "substantial exclusion" is as described above.

The ability to measure the molar flux of the charged redox active material through the membrane during the operation of the flow battery may be conveniently measured for those systems in which each electrolyte comprises a redox active material based on a different metal such as provided in some embodiments described here (e.g., iron in the positive electrolyte and titanium in the negative electrolyte). This may be done by (a) operating such a cell at a fixed temperature (typically ambient room, but also super-ambient, temperatures) for a prescribed period of time (depending on the rate of flux, for example, 1 hour), (b) measuring and quantifying the amount of metal which has passed through the membrane from the source to second electrolyte (using, for example, atomic absorption spectroscopy, inductively coupled plasma, ion chromatography, or other suitable method), and (c) comparing that amount of metal ions with the amount of mobile ion which has passed through the membrane, corresponding to the total electrons which have passed over that period of time. By measuring the flux as a function of time and temperature, and membrane thicknesses, it is also possible to calculate the thermodynamic parameters associated with this particular system, and predict longevity of the system.

These flow batteries of the present invention include those capable of or actually providing excellent round trip current efficiencies. In certain embodiments, the flow batteries described above, when operating, exhibit a round trip current efficiency of at least 98% over a state-of-charge in a range of from about 35 to about 65%. In other independent embodiments, the flow batteries exhibit round trip current efficiency of at least about 98.5, 99, 99.5, or 99.8% over a state-of-charge in a range of from about 35 to about 65%. In still other embodiments, these efficiencies are achieved over a state-of-charge in a range of from about 40 to about 60% or about 50%.

The flow batteries of the present invention also provide superior open circuit potentials and energy densities. In certain independent embodiments, the flow batteries of the present invention exhibit an open circuit potential of at least about 0.8 V, at least about 1.0 V, at least about 1.2 V, at least about 1.4 V, at least about 1.6 V, or at least about 2 V. In other independent embodiments, the flow batteries of the present invention are able to provide an energy density of at least 10 Wh/L, at least about 20 Wh/L, or at least about 30 Wh/L.

To this point, the various embodiments have been described mainly in terms of individual flow batteries. It should be appreciated that, where possible, the descriptions should be read as including flow batteries that are operating or capable of operating with the specified characteristics. Similarly, the descriptions should be read as including systems of flow batteries, wherein the system comprises at least two of the flow batteries described herein.

An exemplary flow battery is shown in FIG. 1. As shown in that figure, a flow battery system may include an electrochemical cell that features a (e.g., a membrane) that separates the two electrodes of the electrochemical cell. Electrode 10 is suitably a conductive material, such as a metal, carbon, graphite, and the like. Tank 50 may contain first redox material 30, which material is capable of being cycled between an oxidized and reduced state.

A pump 60 may effect transport of the first active material 30 from the tank 50 to the electrochemical cell. The flow battery also suitably includes a second tank (not labeled) that contains the second active material 40. The second active material 40 may or may not be the same as active material 30. A second pump (not labeled) may effect transport of second redox material 40 to the electrochemical cell. Pumps may also be used to effect transport of the active materials from the electrochemical cell to the tanks of the system. Other methods of effecting fluid transport—e.g., siphons—may be used to transport redox material into and out of the electrochemical cell. Also shown is a power source or load 70, which completes the circuit of the electrochemical cell and allows the user to collect or store electricity during operation of the cell.

It should be understood that FIG. 1 depicts a specific, non-limiting embodiment of a flow battery. Accordingly, devices according to the present disclosure may or may not include all of the aspects of the system depicted in FIG. 1. As one example, a system according to the present disclosure may include active materials that are solid, liquid, or gas and/or solids, liquids, or gases dissolved in solution, or slurries. Active materials may be stored in a tank, in a vessel open to the atmosphere, or simply vented to the atmosphere.

In some cases, a user may desire to provide higher charge or discharge voltages than available from a single battery. In such cases, and in certain embodiments, then, several batteries are connected in series such that the voltage of each cell is additive. An electrically conductive, but non-porous material (e.g., a bipolar plate) may be employed to connect adjacent battery cells in a bipolar stack, which allows for electron transport but prevents fluid or gas transport between adjacent cells. The positive electrode compartments and negative electrode compartments of individual cells are suitably fluidically connected via common positive and negative fluid manifolds in the stack. In this way, individual electrochemical cells can be stacked in series to yield a voltage appropriate for DC applications or conversion to AC applications.

A region of a cell in a stack will represent a differential element (for example 2-60 $cm^2$) of a larger cell, which has practical areas of approximately 200 to 6000 $cm^2$ for useful devices. This differential element will be characterized by uniform conditions across that area, which includes positive and negative active material and electrolyte concentrations, voltage, and current density. A cell is represented by the entire active area range given above, where non-uniformities may exist in the active material and electrolyte concentrations, voltages, and current density.

In additional embodiments, the cells, cell stacks, or batteries are incorporated into larger energy storage systems, suitably including piping and controls useful for operation of these large units. Piping, control, and other equipment suitable for such systems are known in the art, and include, for example, piping and pumps in fluid communication with the respective electrochemical reaction chambers for moving electrolytes into and out of the respective chambers and storage tanks for holding charged and discharged electrolytes. The energy storage and generation systems described by the present disclosure may also include electrolyte circulation loops, which loops may comprise one or more valves, one or more pumps, and optionally a pressure equalizing line. The energy storage and generation systems of this disclosure can also include an operation management system. The operation management system may be any suitable controller device, such as a computer or microprocessor, and may contain logic circuitry that sets operation of any of the various valves, pumps, circulation loops, and the like.

A suitable flow battery system may comprise a flow battery (including a cell or cell stack); storage tanks and piping for containing and transporting the electrolytes; control hardware and software (which may include safety systems); and a power conditioning unit. The flow battery cell stack accomplishes the conversion of charging and discharging cycles and determines the peak power of energy storage system, which power may in some embodiments be in the kW range. The storage tanks contain the positive and negative active materials; the tank volume determines the quantity of energy stored in the system, which may be measured in kWh. The control software, hardware, and optional safety systems suitably include sensors, mitigation equipment and other electronic/hardware controls and safeguards to ensure safe, autonomous, and efficient operation of the flow battery energy storage system. Such systems are known to those of ordinary skill in the art. A power conditioning unit may be used at the front end of the energy storage system to convert incoming and outgoing power to a voltage and current that is optimal for the energy storage system or the application. For the example of an energy storage system connected to an electrical grid, in a charging cycle the power conditioning unit would convert incoming AC electricity into DC electricity at an appropriate voltage and current for the electrochemical stack. In a discharging cycle, the stack produces DC electrical power and the power conditioning unit converts to AC electrical power at the appropriate voltage and frequency for grid applications.

The energy storage systems of the present disclosure are, in some embodiments, suited to sustained charge or discharge cycles of several hour durations. As such, the systems of the present disclosure may be used to smooth energy supply/demand profiles and provide a mechanism for stabilizing intermittent power generation assets (e.g., from renewable energy sources). It should be appreciated, then, that various embodiments of the present disclosure include those electrical energy storage applications where such long charge or discharge durations are valuable. For example, non-limiting examples of such applications include those where systems of the present disclosure are connected to an electrical grid include, so as to allow renewables integration, peak load shifting, grid firming, baseload power generation consumption, energy arbitrage, transmission and distribution asset deferral, weak grid support, frequency regulation, or any combination thereof. Cells, stacks, or systems according to the present disclosure may be used to provide stable power for applications that are not connected to a grid, or a micro-grid, for example as power sources for remote camps, forward operating bases, off-grid telecommunications, remote sensors, or any combination thereof.

Flow battery energy storage efficacy is determined by both the round trip DC-DC energy efficiency ($RT_{EFF}$) and the energy density of the active materials (measured in Wh/L). The $RT_{EFF}$ is a composite of voltage and current efficiencies for both the battery charge and discharge cycles. In electrochemical devices, voltage and current efficiencies are functions of the current density, and while voltage and current efficiency typically decrease as current density (mA/cm$^2$) increases, high current densities are often desirable to reduce electrochemical stack size/cost used to achieve a given power rating. Active material energy density is directly proportional to the cell OCV (OCV=open circuit voltage), the concentration of active species, and the number of electrons transferred per mole of active species. High energy densities are desirable to reduce the volume of active materials required for a given quantity of stored energy.

It should be appreciated that, while the various embodiments described herein are described in terms of flow battery systems, the same strategies, designs, chemical embodiments, and combinations thereof, may also be employed with stationary (non-flow) electrochemical cells, batteries, or systems, including those where one or both half cells employ stationary electrolytes. Each of these embodiments is considered within the scope of the present invention.

Terms

Throughout this specification, words are to be afforded their normal meaning, as would be understood by those skilled in the relevant art. However, so as to avoid misunderstanding, the meanings of certain terms will be specifically defined or clarified.

The term "active material" is well known to those skilled in the art of electrochemistry and electrochemical energy storage and is meant to refer to materials which undergo a change in oxidation state during operation of the system. Active materials may comprise a solid, liquid, or gas and/or solids, liquids, or gasses dissolved in solution. In some embodiments, active materials comprise molecules, supramolecules, or any combination thereof, dissolved in solution. The concentration of these active materials may be greater than 2 M, between 1 and 2 M, about 1.5 M, between 0.5 M and 1 M, or even less than 0.5 M.

Suitable active material may comprise a "metal ligand coordination compound." Suitable metal ligand coordination compounds are known to those skilled in the art of electrochemistry and inorganic chemistry. A metal ligand coordination compound may comprise a metal ion bonded to an atom or molecule. The bonded atom or molecule is referred to as a "ligand". In certain non-limiting embodiments, the ligand may comprise a molecule comprising C, H, N, and/or O atoms. In other words, the ligand may comprise an organic molecule. The metal ligand coordination compounds of the present disclosure are understood to comprise at least one ligand that is not water, hydroxide, or a halide ($F^-$, $Cl^-$, $Br^-$, $I^-$).

Metal ligand coordination compounds may comprise a "redox active metal ion" and/or a "redox inert metal ion". The term "redox active metal ion" is intended to connote that the metal undergoes a change in oxidation state under the conditions of use. As used herein, the term "redox inert" metal ion is intended to connote that the metal does not undergo a change in oxidation state under the conditions of use. Metal ions may comprise non-zero valence salts of, e.g., Al, Ca, Co, Cr, Sr, Cu, Fe, Mg, Mn, Mo, Ni, Pd, Pt, Ru, Sn, Ti, Zn, Zr, V, U or a combination thereof. The skilled artisan would be able to recognize the circumstances where a given non-zero valence metal would be redox active or inactive under the prescribed electrolyte environments.

Suitable active materials may comprise an "organic active material". An organic active material may comprise a molecule or supramolecule that does not contain a transition metal ion. It is further understood that organic active materials are meant to comprise molecules or supramolecules that are dissolved in aqueous solution. Suitable organic active materials are capable of undergoing a change in oxidation state during operation of the electrochemical energy storage system. Accordingly, the molecule or supramolecule may accept or donate an electron during operation of the system.

The terms "a catecholate," "a glycolate," "a polyol", "a hydroxyalkanoate", "a benzoate", "a phthalate", "a urea" and "a polyamine" reflect the fact that these ligands may be optionally substituted with at least one group independently selected from H, $C_{1-6}$ alkoxy, $C_{1-6}$ alkyl, $C_{1-6}$ alkenyl, $C_{1-6}$ alkynyl, 5-6 membered aryl or heteroaryl, a boric acid or a salt thereof, carboxy acid or a salt thereof, cyano, halo, hydroxyl, nitro, sulfonate, sulfonic acid or a salt thereof, phosphonate, phosphonic acid or a salt thereof, or a polyglycol (preferably polyethylene glycol).

Alkaneoate includes alpha, beta, and gamma forms. Polyamine includes, but is not limited to, ethylene diamine, ethylene diamine tetraacetic acid (EDTA), and diethylene triamine pentaacetic acid (DTPA). Catecholeate includes all compositions comprising a 1,2-dihydroxybenzene moiety. Such moieties include hydroxycatecholates (including pyrogallate), as well as substitutents listed herein. Substituents include, but are not limited to, alkyl, alkenyl, and alkynyl (each refer to branched or linear structures and structures optionally substituted with one or more carboxyl, halo, hydroxyl or other electron withdrawing or electron donating groups. Substituents also include 5-6 membered aryl or heteroaryls include phenyl, pyridinyl, furyl, pyrrolyl, imidazolyl, triazole, or thiophenyl. Electron withdrawing or donating substituents can be added to the periphery of the aromatic rings to modulate the redox potential of the redox active ligands.

Unless otherwise specified, the term "aqueous" refers to a solvent system comprising at least about 98% by weight of water, relative to total weight of the solvent. In some applications, soluble, miscible, or partially miscible (emulsified with surfactants or otherwise) co-solvents may also be usefully present which, for example, extend the range of water's liquidity (e.g., alcohols/glycols). When specified, additional independent embodiments include those where the "aqueous" solvent system comprises at least about 55%, at least about 60 wt %, at least about 70 wt %, at least about 75 wt %, at least about 80%, at least about 85 wt %, at least about 90 wt %, at least about 95 wt %, or at least about 98 wt % water, relative to the total solvent. It some situations, the aqueous solvent may consist essentially of water, and be substantially free or entirely free of co-solvents or other species. The solvent system may be at least about 90 wt %, at least about 95 wt %, or at least about 98 wt % water, and, in some embodiments, be free of co-solvents or other species.

In addition to the redox active materials described below, the aqueous electrolytes may contain additional buffering agents, supporting electrolytes, viscosity modifiers, wetting agents, and the like.

The term "bipolar plate" refers to an electrically conductive, substantially nonporous material that may serve to separate electrochemical cells in a cell stack such that the cells are connected in series and the cell voltage is additive across the cell stack. The bipolar plate has two surfaces such that one surface of the bipolar plate serves as a substrate for the positive electrode in one cell and the negative electrode in an adjacent cell. The bipolar plate typically comprises carbon and carbon containing composite materials.

The term "cell geometry" is well known to those of ordinary skill in the art of electrochemistry and refers to the over physical construction of the flow battery.

The term "cell mechanical loading" is well known to those of ordinary skill in the art of electrochemistry and refers to the degree of mechanical compression that is experienced in an individual flow battery cell or, on an average basis by an individual cell in a stack of cells. The degree of mechanical compression is normally measured in psi.

The term "cell potential" is readily understood by those skilled in the art of electrochemistry and is defined to be the voltage of the electrochemical cell during operation. The cell potential may be further defined by Equation 1:

$$\text{Cell Potential} = OCV - \eta_{pos} - \eta_{neg} - iR \quad (1)$$

where OCV is the "open circuit potential", $\eta_{pos}$ and $\eta_{neg}$ are the overpotentials for the positive and negative electrodes at a given current density, respectively, and iR is the voltage loss associated with all cell resistances combined. The "open circuit potential" or OCV may be readily understood according to Equation 2:

$$OCV = E^+ - E^- \quad (2)$$

where $E^+$ and $E^-$ are the "half-cell potentials" for the redox reactions taking place at the positive and negative electrodes, respectively. The half-cell potentials may be further described by the well-known Nernst Equation 3:

$$E = E^0 - RT/nF \ln(X_{red}/X_{ox}) \quad (3)$$

wherein $E^0$ is the standard reduction potential for redox couple of interest (e.g. either the positive or negative electrode), the R is the universal gas constant, T is temperature, n is the number of electrons transferred in the redox couple of interest, F is Faraday's constant, and $X_{red}/X_{ox}$ is the ratio of reduced to oxidized species at the electrode.

The term "current density" refers to the total current passed in an electrochemical cell divided by the geometric area of the electrodes of the cell and is commonly reported in units of mA/cm$^2$.

The term "current efficiency" ($I_{EFF}$) may be described as the ratio of the total charge produced upon discharge of the system to the total charge passed upon charge. In some embodiments, the charge produced on discharge or passed on charge can be measured using standard electrochemical coulomb counting techniques well known to those of ordinary skill in the art. Without being bound by the limits of any theory, the current efficiency may be a function of the state of charge of the flow battery. In some non-limiting embodiments the current efficiency can be evaluated over an SOC range of about 35% to about 60%.

The term "diffusion media properties" is well known to those of ordinary skill in the art of electrochemistry and refers to the properties of a material that allow ions or molecules to diffuse across that material.

The term "energy density" refers to the amount of energy that may be stored, per unit volume, in the active materials. Energy density, as used herein, refers to the theoretical energy density of energy storage and may be calculated by Equation 4:

$$\text{Energy density} = (26.8 \text{ A-h/mol}) \times OCV \times [e^-] \quad (4)$$

where OCV is the open circuit potential at 50% state of charge, as defined above, (26.8 A-h/mol) is Faraday's constant, and $[e^-]$ is the concentration of electrons stored in the active material at 99% state of charge. In the case that the active materials largely comprise an atomic or molecular species for both the positive and negative electrolyte, $[e^-]$ may be calculated as:

$$[e^-] = [\text{active materials}] \times n/2 \quad (5)$$

where [active materials] is the concentration (mol/L or M) of the active material in either the negative or positive electrolyte, whichever is lower, and n is the number of electrons transferred per molecule of active material. The related term "charge density" refers to the total amount of charge that each electrolyte may contain. For a given electrolyte:

$$\text{Charge density} = (26.8 \text{ A-h/mol}) \times [\text{active material}] \times n \quad (6)$$

where [active material] and n are as defined above.

The term "energy efficiency" may be described as the ratio of the total energy produced upon discharge of the system to the total energy consumed upon charge. The energy efficiency ($RT_{EFF}$) may be computed by Equation 7:

$$RT_{EFF} = V_{EFF,RT} \times I_{EFF} \quad (7)$$

As used herein, the term "evolution current" describes the portion of the electrical current applied in an energized flow battery configuration which is associated with the evolution (generation) of a particular chemical species. In the current context, then, when a sufficient overpotential vide infra) is applied in a flow battery such that either or both oxygen evolves at the positive electrode or hydrogen evolves at the negative electrode, that portion of the current associated with the evolution of oxygen or hydrogen is the oxygen evolution current or hydrogen evolution current, respectively.

In certain preferred embodiments, there is no current associated with hydrogen evolution, oxygen evolution, or both hydrogen and oxygen evolution. This may occur when the positive half-cell is operating at a potential less than the thermodynamic threshold potential or the threshold overpotential of the positive electrode (i.e., no oxygen produced; see explanation of terms below) or the negative half-cell cell is operating at a potential more positive than the thermodynamic threshold potential or the threshold overpotential of the negative electrode (i.e., no hydrogen produced), or both.

In separate embodiments, the batteries operate within 0.3 V, within 0.25 V, within 0.2 V, within 0.15 V, or within 0.1 V of either the thermodynamic threshold potential or the threshold overpotential of the respective positive or negative electrodes.

In embodiments wherein gas is evolved, the portion of current associated with gas evolution (either hydrogen or oxygen or both) is suitably less than about 20%, less than about 15%, less than about 10%, less than about 5%, less than about 2%, or less than about 1% of the total applied current. Lower gas evolution currents are considered particularly suitable for battery (cell or cell stack) efficiencies.

The term "excluding" refers to the ability of a separator to not allow certain ions or molecules to flow through the separator and typically is measured as a percent.

The term "mobile ion" is understood by those skilled in the art of electrochemistry and is meant to comprise the ion which is transferred between the negative and positive electrode during operation of the electrochemical energy storage system. The term "mobile ion" may also refer to as an ion that carries greater than at least 80% of the ionic current during charger/discharge.

As used herein, the terms "negative electrode" and "positive electrode" are electrodes defined with respect to one another, such that the negative electrode operates or is designed or intended to operate at a potential more negative than the positive electrode (and vice versa), independent of the actual potentials at which they operate, in both charging and discharging cycles. The negative electrode may or may not actually operate or be designed or intended to operate at a negative potential relative to the reversible hydrogen electrode. The negative electrode is associated with the first aqueous electrolyte and the positive electrode is associated with the second electrolyte, as described herein.

The term "overpotential" is well understood by those skilled in the art of electrochemistry and is defined by the difference in voltage between an electrode during operation of an electrochemical cell and the normal half-cell potential of that electrode, as defined by the Nernst equation. Without being bound by theory, the term overpotential is meant to describe the energy, in excess of that required by thermodynamics, to carry out a reaction at a given rate or current density. The term "overpotential" also describes a potential more positive than the thermodynamic onset voltage for oxygen evolution from water at the positive electrode and more negative than the thermodynamic onset voltage for hydrogen evolution from water at the negative electrode.

Similarly, as used herein, the term "threshold overpotential" refers to the overpotential at which either hydrogen or oxygen gas begins to evolve at the respective electrode. Note that an electrochemical system comprising "imperfect" (i.e., less than ideal catalytically) electrodes can be operated in three regions: (a) at a potential "below" the thermodynamic onset potential (i.e., more positive than the thermodynamic onset potential of the negative electrode and more negative than the thermodynamic onset potential of the positive electrode; no gas evolving so no gas evolution current); (b) at a potential between the thermodynamic threshold potential and threshold overpotential (no gas evolving and still no evolution current); and (c) beyond the threshold overpotential (gas evolving and exhibiting a gas evolution current). Such threshold overpotentials can be identified by those skilled in the art for a given system, for example, by measuring gas evolution as a function of applied half-cell potential (using e.g., a mass spectrometer), in the presence or absence of an electroactive material. See also below.

The gas evolution threshold potentials are also affected by the nature of the electrolytes. Certain chemicals are known to inhibit the evolution of hydrogen and oxygen in electrolytic cells, either because of some activity in the bulk electrolyte or because of their ability to coat or otherwise deactivate their respective electrodes; for example, macromolecules or oligomers or salts, such as chloride or phosphate, on Pt surfaces. Accordingly, in certain embodiments, then, either the first or second or both first and second electrolytes comprise at least one compound increases the hydrogen or oxygen threshold overpotential of the system, respectively.

As used herein, the terms "regenerative fuel cell" or "reversible fuel cell" or "flow battery" or "flow energy device" connote the same or similar type of device, which utilizes the same battery configuration (including cell or cell stack) for both energy storage and energy generation.

The term "reversible hydrogen electrode," or RHE, is used in its conventional meaning. That is, a reversible hydrogen electrode (RHE) is a reference electrode. The potential of the RHE, E(RHE) corresponds to the potential for the reaction of Equation 8:

$$2H^+ \leftrightarrow H_2 \tag{8}$$

When the reaction of Equation 8 is carried out at equilibrium at a given pH and 1 atm $H_2$. This potential can be reference to a normal hydrogen electrode, E(NHE), by the following relation:

$$E(\text{RHE}) = E(\text{NHE}) - 0.059 \times \text{pH} = 0.0 \text{ V} - 0.059 \times \text{pH} \tag{9}$$

where E(NHE) is the potential for the normal hydrogen electrode (NHE=0.0V), defined as the potential for the reaction of Equation 8 at standard state (1M $H^+$, 1 atm $H_2$). Thus a potential of 0 V vs. RHE corresponds to a voltage of 0 V vs. NHE at pH 0 and −0.413 V vs. NHE at pH 7.

The term "selectivity" is well known to those of ordinary skill in the art of electrochemistry and refers to the ability of a membrane to allow a ratio of the movement of mobile ions to active materials through a membrane. For example, a membrane that allows a 50:1 ratio of mobile ions to active materials to pass through would have a selectivity of 50.

The terms "separator" and "membrane" refer to an ionically conductive, electrically insulating material disposed between the positive and negative electrode of an electrochemical cell.

The polymer electrolytes useful in the present disclosure may be anion or cation conducting electrolytes. Where described as an "ionomer," the term refers to a polymer comprising both electrically neutral and a fraction of ionized repeating units, wherein the ionized units are pendant and covalently bonded to the polymer backbone. The fraction of ionized units may range from about 1 mole percent to about 90 mole percent, but may be further categorized according to their ionized unit content. For example, in certain cases, the content of ionized units are less than about 15 mole percent; in other cases, the ionic content is higher, typically greater than about 80 mole percent. In still other cases, the ionic content is defined by an intermediate range, for example in a range of about 15 to about 80 mole percent. Ionized ionomer units may comprise anionic functional groups comprising sulfonate, carboxylate, and the like. These functional groups can be charge balanced by, mono-, di-, or higher-valent cations, such as alkali or alkaline earth metals. Ionomers may also include polymer compositions containing attached or embedded quaternary ammonium, sulfonium, phosphazenium, and guanidinium residues or salts. The polymers useful in the present disclosure may comprise highly fluorinated or perfluorinated polymer backbones. Certain polymer electrolytes useful in the present disclosure include copolymers of tetrafluoroethylene and one or more fluorinated, acid-functional co-monomers, which are commercially available as NAFION™ perfluorinated polymer electrolytes from DuPont Chemicals, Wilmington Del. Other useful perfluorinated electrolytes comprise copolymers of tetrafluoroethylene (TFE) and $FSO_2$—$CF_2CF_2CF_2CF_2$—O—CF=$CF_2$.

The term "stack" or "cell stack" or "electrochemical cell stack" refers to a collection of individual electrochemical cells that are in electrically connected. The cells may be electrically connected in series or in parallel. The cells may or may not be fluidly connected.

The term "state of charge" (SOC) is determined from the concentration ratio of reduced to oxidized species at an electrode ($X_{red}/X_{ox}$). For example, in the case of an individual half-cell, when $X_{red}=X_{ox}$ such that $X_{red}/X_{ox}=1$, the half-cell is at 50% SOC, and the half-cell potential equals the standard Nerstian value, E°. When the concentration ratio at the electrode surface corresponds to $X_{red}/X_{ox}=0.25$ or $X_{red}/X_{ox}=0.75$, the half-cell is at 25% and 75% SOC respectively. The SOC for a full cell depends on the SOCs of the individual half-cells and in certain embodiments the SOC is the same for both positive and negative electrodes. Measurement of the cell potential for a battery at OCV, and using Equations 2 and 3 the ratio of $X_{red}/X_{ox}$ at each electrode can be determined, and therefore the SOC for the battery system.

The term "supporting electrolyte" is well-known in the arts of electrochemistry and energy storage, and is intended to refer to any species which is redox inactive in the window of electric potential of interest and aids in supporting charge and ionic conductivity. In the present case, a supporting electrolyte does not substantially compromise the solubility of the coordination complex. Non-limiting examples include salts comprising an alkali metal, ammonium ion including an ammonium ion partially or wholly substituted by alkyl or aryl groups, halide (e.g., $Cl^-$, $Br^-$, $I^-$), chalcogenide, phosphate, hydrogen phosphate, phosphonate, nitrate, sulfate, nitrite, sulfite, perchlorate, tetrafluoroborate, hexafluorophosphate, or a mixture thereof, and others known in the art.

The term "voltage efficiency" may be described as the ratio of the observed electrode potential, at a given current density, to the half-cell potential for that electrode (×100%), wherein the half-cell potential is calculated as described above. Voltage efficiencies can be described for a battery charging step, a discharging step, or a "round trip voltage efficiency". The round trip voltage efficiency ($V_{EFF,RT}$) at a given current density can be calculated from the cell voltage at discharge ($V_{Discharge}$) and the voltage at charge ($V_{charge}$) using Equation 10:

$$V_{EFF,RT}=V_{Discharge}/V_{Charge}\times 100\% \quad (10)$$

Exemplary Operating Characteristics

The present disclosure provides a variety of technical features of the disclosed systems and methods. It should be understood that any one of these features may be combined with any one or more other features. For example, a user might operate a system featuring an electrolyte that includes an organic active material (e.g., a quinone), wherein that electrode has a pH of about 3. Such a system might also feature a membrane separator having a thickness of about 35 micrometers. It should be further understood that the present disclosure is not limited to any particular combination or combinations of the following features.

Certain embodiments of the present invention provides method of operating a flow battery, each method comprising charging said battery by the input of electrical energy or discharging said battery by the removal of electrical energy. Further embodiments provide applying a potential difference across the first and second electrode, with an associated flow of electrons, so as to: (a) reduce the first redox active material while oxidizing the second redox active material; or (b) oxidize the first redox active material while reducing the second redox active material. Complementary methods provide those where each method comprises applying a potential difference across the first and second electrode, with an associated flow of electrons, so as to: (a) oxidize the first redox active metal-ligand coordination compound; or (b) reduce the second redox active metal-ligand coordination compound; or (c) both (a) and (b).

Mobile ions typically include proton, hydronium, or hydroxide. In various embodiments of the present disclosure, one may additionally transport ions other than proton, hydronium, or hydroxide (e.g., when these ions are present in comparatively low concentration, such as below 1 M). Separate embodiments of these methods of operating a flow battery include those wherein the mobile ion does not consist essentially of protons, hydronium, or hydroxide. In this embodiment, less than 50% of the mobile ions comprise protons, hydronium, or hydroxide. In other embodiments, less than about 40%, less than about 30%, less than about 20%, less than about 10%, less than about 5%, or less than about 2% of the mobile ions comprise protons, hydronium, or hydroxide. Exemplary mobile ions in these embodiments include alkali metal or alkaline earth metal cations (especially $Li^+$, $Na^+$, $K^+$, $Mg^{2+}$, $Ca^{2+}$, $Sr^{2+}$), halides (e.g., $F^-$, $Cl^-$, or $Br^-$), or $OH^-$.

In some embodiments of the present disclosure, it is advantageous to operate between pH 1 and 13 (e.g. to enable active material solubility and/or low system cost). Accordingly, one or both electrolytes can be characterized as having a pH in the range of from about 1 to about 13, or between about 2 and about 12, or between about 4 and about 10, or even between about 6 and about 8. In other embodiments, at least one of the electrolytes has a pH in a range of from about 9 to about 13, from about 8 to about 12, from about 10 to about 12, or from 10.5 to about 11.5. For the most part, the compounds described herein comprising catecholate or pyrogallate are stable and operable at pH's within each of the ranges described herein. Generally, the compounds described herein are stable and operable at pH's within each of these ranges. In some embodiments, the pH of the electrolyte may be maintained by a buffer. Typical buffers include salts of phosphate, borate, carbonate, silicate, tris (hydroxymethyl)aminomethane (Tris), 4-(2-hydroxyethyl)-1-piperazineethanesulfonic acid (HEPES), piperazine-N,N'-bis(ethanesulfonic acid) (PIPES), and combinations thereof. A user may add an acid (e.g., HCl, $HNO_3$, $H_2SO_4$ and the like), a base (NaOH, KOH, and the like), or both to adjust the pH of a given electrolyte as desired.

The pH of the first and second electrolytes may suitably be equal or substantially similar; in other embodiments, the pH of the two electrolytes differ by a value in the range of about 0.1 to about 2 pH units, about 1 to about 10 pH units, about 5 to about 12 pH units, about 1 to about 5 pH units, about 0.1 to about 1.5 pH units, about 0.1 to about 1 pH units, or about 0.1 to about 0.5 pH units. In this context, the term "substantially similar," without further qualification, is intended to connote that the difference in pH between the two electrolytes is less than about 1 pH unit. Additional optional embodiments provide that the pH difference is less than about 0.4, less than about 0.3, less than about 0.2, or less than about 0.1 pH units.

The disclosed systems and methods may also comprise active materials and membrane ionomers which are charged. The term "charge" in refers to the "net charge" or total charge associated with an active material or ionomer moiety. The charged species may be anionic or cationic. In certain desired embodiments of the present disclosure it is advantageous for the active materials and membrane ionomers to comprise charges of the same sign (e.g. to prevent transfer of the active material across the membrane).

Systems and methods according to the present disclosure also feature active materials comprising metal-ligand coordination compounds. Metal-ligand coordination compounds may be present at, e.g., a concentration of at least about 0.25 M, at least about 0.35 M, at least about 0.5 M, at least about 0.75 M, at least about 1 M, at least about 1.25 M, at least about 1.5 M, at least about 2 M, or greater than 2 M.

The metal-ligand coordination compound may be further characterized with respect to the nature of the oxidizable or reducible species. For example, in some cases, the redox potential of the metal-ligand coordination compound may be defined by transitions entirely within the metal center—i.e., the redox potential is defined by the accessibility of and energies associated with transitions between various valence states within the metal. In other cases, the oxidation/reduction may be localized within the ligand system. In still other cases, the oxidation/reduction may be distributed throughout the entire redox active complex, such that both the metal and the ligand system sharing in the distribution of charge. Preferably, the redox potential should differ by at least 0.5 volt. More preferably, the redox potential should differ by at least 1.0 volt. It is suitable for each electrolyte to contain the same metal center, so long as the first metal center and second metal center have different oxidation states.

In particular embodiments of the present disclosure, the metal-ligand coordination compound may comprise ligands which are mono-, bi-, tri-, or multidentate. Monodentate ligands bind to metals through one atom, whereas bi-, tri-, or multidentate ligands bind to metals through 2, 3, or more atoms, respectively. Examples of monodentate ligands include halogens ($F^-$, $Cl^-$, $Br^-$, $I^-$), cyanide (CN), carbonyl or carbon monoxide (CO), nitride ($N^{3-}$), oxo ($O^{2-}$), hydroxo (OH), water ($H_2O$), sulfide ($S^{2-}$), pyridine, pyrazine, and the like. Other types of ligand bonding moieties include amino groups ($NR_3$), amido groups ($N(R)_2$), imido groups (NR), alkoxy groups ($R—CO^-$), siloxy ($R—SiO^-$), thiolate ($R—S^-$), and the like, which may comprise mono-, bi-, tri-, or multidentate ligands. Examples of bidentate ligands include catechol, bipyridine, bipyrazine, ethylenediamine, diols (including ethylene glycol), and the like. Examples of tridentate ligands include terpyridine, diethylenetriamine, triazacyclononane, trisaminomethane, and the like. Other acceptable ligands include quinones, hydroquinones, viologens, pyridinium, acridinium, polycyclic aromatic hydrocarbons and combinations thereof.

In other embodiments, the first or second redox active material, or both the first and second redox active materials comprise a metal ligand coordination compound of the formula $M(L1)_{3-x-y}(L2)_x(L3)_y^m$, where M is independently a non-zero valent metal or metalloid of Groups 2-16, including lanthanides and actinides, where x and y are independently 0, 1, 2, or 3, such that 3-x-y is not less than zero;
m is independently −5, −4, −3, −2, −1, 0, 1, 2, 3, 4, or 5; and
L1, L2, and L3 are each independently ascorbate, citrate, gluconate, lactate, or a compound having structure according to Formula I, or an oxidized or reduced form thereof:

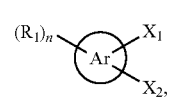

wherein
Ar is a 5-20 membered aromatic moiety, optionally comprising one of more ring O, N, or S heteroatoms;
$X_1$ and $X_2$ are independently —OH, —$NHR_2$, —SH, or an anion thereof, $X_1$ and $X_2$ being positioned ortho to one another;
$R_1$ is independently at each occurrence H, $C_{1-6}$ alkoxy, $C_{1-6}$ alkyl, $C_{1-6}$ alkenyl, $C_{1-6}$ alkynyl, 5-6 membered aryl or heteroaryl, a boric acid or a salt thereof, carboxy acid or a salt thereof, carboxylate, cyano, halo, hydroxyl, nitro, sulfonate, sulfonic acid or a salt thereof, phosphonate, phosphonic acid or a salt thereof, or a polyglycol (preferably polyethylene glycol);
$R_2$ is independently H or $C_{1-3}$ alkyl; and
n is 0, 1, 2, 3, 4, 5, 6, 7, 8, 9, or 10.

In other embodiments, the first redox active material comprises a metal ligand coordination complex of the formula $M(L1)_{3-x-y}(L2)_x(L3)_y^m$ and x and y are independently 0, 1, 2, or 3, such that 3-x-y is not less than zero;
m is −5, −4, −3, −2, −1, 0, 1, 2, 3, 4, or 5; and
M is Al, Cr, Fe, or Ti; and
L1, L2, and L3 are each independently ascorbate, a catecholate, a pyrogallolate, lactate, gluconate, or citrate. The terms "a catecholate" and "a pyrogallolate" reflect the fact that these ligands may be optionally substituted with at least one $R_1$ group, as defined above—i.e., in independent embodiments, the catecholate or pyrogallate are substituted and unsubstituted.

Some embodiments provide certain separator characteristics, both in absolute compositional and parametric terms and in relation to the metal ligand coordination compounds. Other embodiments describe specific functional characteristics which derive from the inventive systems.

In still other embodiments, the second redox active material comprises a metal ligand coordination complex of the formula $M(L1)_{3-x-y}(L2)_x(L3)_y^m$,
M comprises Al, Ca, Ce, Co, Cr, Fe, Mg, Mo, S, Sn, Ti, U, W, Zn, or Zr;
L1, L2, and L3 are each independently ascorbate, a catecholate, a pyrogallate, lactate, gluconate, or citrate;
x and y are independently 0, 1, 2, or 3, such that 3-x-y is not less than 0;
and m is −2, −3, −4, or −5. Related embodiments provide that if x is 0, y is not 0.

Either or both of the electrodes that carry out the electrochemical reactions may comprise carbon and either or both of the first and second metal ligand coordination compound independently exhibits substantially reversible electrochemical kinetics. Similarly, in either case, separate independent embodiments provide that if x is 0, y is not 0.

In those embodiments where the first and second aqueous electrolytes each comprises a first and second metal ligand coordination compound, respectively, the first and second metal ligand coordination compounds may be the same or different, though preferably they are different.

The invention also provides those embodiments were either the first or the second or both the first and second metal ligand coordination compound comprises at least one ligand having a structure according to Formula I. Similarly, either or both of the metal ligand coordination compounds may comprise at least one ligand having a structure according to Formula IA, IB, or IC:

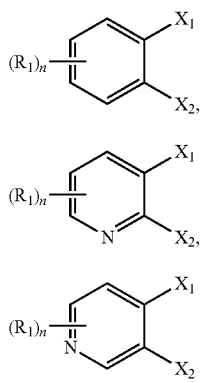

wherein
$X_1$ and $X_2$ are independently —OH, —$NHR_2$, —SH, or an anion thereof;
$R_1$ is independently H, $C_{1-3}$ alkoxy, $C_{1-3}$ alkyl, a boric acid or a salt thereof, a boric acid or a salt thereof, carboxy acid or a salt thereof, carboxylate, cyano, halo, hydroxyl, nitro, sulfonate, sulfonic acid or a salt thereof, phosphonate, phosphonic acid or a salt thereof, or a polyglycol (preferably polyethylene glycol)
$R_2$ is independently H or $C_{1-3}$ alkyl; and
n is 0, 1, 2, 3, or 4.

Additional embodiments provide either or both of the metal ligand coordination compounds comprises at least one ligand having a structure according to Formula IA, IB, or IC, but where:
$X_1$ and $X_2$ are both OH or an anion thereof;
$R_1$ is independently H, $C_{1-3}$ alkoxy, a boric acid or a salt thereof, a boric acid or a salt thereof, carboxy acid or a salt thereof, carboxylate, cyano, halo, hydroxyl, nitro, sulfonate, sulfonic acid or a salt thereof, phosphonate, phosphonic acid or a salt thereof, or a polyglycol (preferably polyethylene glycol); and
n is 1.

In various embodiments, either each or both of the first or second metal ligand coordination compound may also comprise at least one ascorbate, a catecholate, citrate, gluconate, lactate, or a pyrogallate ligand.

The disclosed systems and methods may feature electrochemical cell separators and/or membranes that have certain characteristics. In this disclosure, the terms membrane and separator are used interchangeably. The membranes of the present disclosure may, in some embodiments, feature a membrane separator having a thickness of less than about 500 micrometers, less than about 300 micrometers, less than about 250 micrometers, less than about 200 micrometers, less than about 100 micrometers, less than about 75 micrometers, less than about 50 micrometers, less than about 30 micrometers, less than about 25 micrometers, less than about 20 micrometers, less than about 15 micrometers, or less than about 10 micrometers. Suitable separators include those separators in which the flow battery is capable of operating with a current efficiency of greater than about 85% with a current density of 100 $mA/cm^2$ when the separator has a thickness of 100 micrometers. More preferably, the flow battery is capable of operating at a current efficiency of greater than 99.5% when the separator has a thickness of less than about 50 micrometers, a current efficiency of greater than 99% when the separator has a thickness of less than about 25 micrometers, and a current efficiency of greater than 98% when the separator has a thickness of less than about 10 micrometers. Suitable separators include those separators in which the flow battery is capable of operating at a voltage efficiency of greater than 60% with a current density of 100 $mA/cm^2$. More preferably, suitable separators include those separators in which the flow battery is capable of operating at a voltage efficiency of greater than 70%, greater than 80% or even greater than 90%.

Separators are generally categorized as either solid or porous. Solid membranes typically comprise an ion-exchange membrane, wherein an ionomer facilitates mobile ion transport through the body of the polymer. It is suitable for the ionomer to have an ionomer mass content on an areal basis of less than $2 \times 10^{-3}$ g ionomer/$cm^2$. The facility with which ions conduct through the membrane can be characterized by a resistance, typically an area resistance in units of $\Omega cm^2$. The area resistance is a function of inherent membrane conductivity and the membrane thickness. Thin membranes are desirable to reduce inefficiencies incurred by ion conduction and therefore can serve to increase voltage efficiency of the energy storage device. Active material crossover rates are also a function of membrane thickness, and typically decrease with increasing membrane thickness. Crossover represents a current efficiency loss that is generally balanced with the voltage efficiency gains by utilizing a thin membrane.

The ability to measure the permeability of the charged redox active material through a given membrane in the absence of charge passing through the flow battery may be conveniently measured, for example, by (a) providing a two chamber cell, each chamber separated by the suitable membrane or separator of a specified thickness, filling each chamber with an electrolyte composition, the first electrolyte containing the metal ligand coordination complex of interest and the second devoid of such complex; (b) maintaining the chamber at a constant temperature (e.g., in a range of from about 20° C. to about 85° C.) for a time suitable for the system (e.g., in a range of from about 1 hour to about 120 hours); (c) measuring and quantifying the amount of metal ligand coordination complex which has passed through the membrane from the first to the second electrolyte (using, for example, atomic absorption or UV-Vis spectroscopy, ion chromatography, or other suitable method); and then (d) calculating the amount of metal ligand coordination complex which has passed through the membrane area over that period of time. By varying the time and temperature of such tests, as well as the membrane thicknesses, it is also possible to calculate the thermodynamic parameter associated with this particular system, and predict longevity of the system.

It is preferred that the first electrolyte substantially comprises the first active material and be substantially free of the second active material, and that second electrolyte substantially comprises the second active material and be substantially free of the first active material, but over time, the concentration of the first active material may increase in the second electrolyte and the concentration of the second active material may increase in the first electrolyte. Suitable flow batteries include batteries where the first active material is present in the second electrolyte at a concentration no greater than about 0.05 M. Conversely, the second active material may be present in the first electrolyte at a concentration no greater than about 0.05 M. Preferably, the concentration of the first active material is present in the second electrolyte and the second active material is present in the first electrolyte at a concentration of not greater than about 0.01 M, or no greater than about 0.001 M or substantially free of the active materials. The diffusion rate of the either the first or second active material through the membrane should be less than about $1\times10^{-5}$ mol cm$^{-2}$ day$^{-1}$, less than about $1\times10^{-6}$ mol cm$^{-2}$ day$^{-1}$, less than about $1\times10^{-2}$ mol cm$^{-2}$ day$^{-1}$, less than about $1\times10^{-9}$ mol cm$^{-2}$ day$^{-1}$, less than about $1\times10^{-11}$ mol cm$^{-2}$ day$^{-1}$, less than about $1\times10^{-13}$ mol cm$^{-2}$ day$^{-1}$, or less than about $1\times10^{-15}$ mol cm$^{-2}$ day$^{-1}$.

Porous membranes are non-conductive membranes which allow charge transfer between two electrodes via open channels filled with conductive electrolyte. Porous membranes are permeable to liquid or gaseous chemicals. This permeability increases the probability of chemicals passing through porous membrane from one electrode to another causing cross-contamination and/or reduction in cell energy efficiency. The degree of this cross-contamination depends on, among other features, the size (the effective diameter and channel length), and character (hydrophobicity/hydrophilicity) of the pores, the nature of the electrolyte, and the degree of wetting between the pores and the electrolyte.

The pore size distribution is generally sufficient to substantially prevent the crossover of active materials between the two electrolyte solutions. Suitable porous membranes will have an average size distribution of between about 0.001 nm and 20 micrometers. Preferably, the average size distribution should be between about 0.001 nm and 100 nm. The size distribution of the pores in a porous membrane can be substantial. In other words, a porous membrane may contain a plurality of pores with a very small diameter (approximately less than 1 nm) and may contain a plurality of pores with a very large diameter (approximately greater than 10 micrometers). The larger pore sizes can lead to a higher amount of active material crossover. The ability for a porous membrane to substantially prevent the crossover of active materials will depend on the relative difference in size between the average pore size and the active material. For example, when the active material is a metal center in the form of a metal-ligand complex, the average diameter of the metal ligand complex is about 50% greater than the average pore size of the porous membrane. On the other hand, if the porous membrane has substantially uniform pore sizes, it is preferred that the average diameter of the metal ligand complex be about 20% larger than the average pore size of the porous membrane. Likewise, the average diameter of a metal ligand complex is increased when the metal-ligand complex is further coordinated with at least one water molecule. The diameter of the metal-ligand complex coordinated with at least one water molecule is generally considered to be the hydrodynamic diameter. In such a situation, the hydrodynamic diameter is generally at least about 35% greater than the average pore size. When the average pore size is substantially uniform, the hydrodynamic radius should be about 10% greater than the average pore size. One of ordinary skill in the art will understand the term "substantially uniform."

Suitable ion-exchange separators may also comprise membranes, which are sometimes referred to as polymer electrolyte membrane (PEM) or ion conductive membrane (ICM). Suitable membranes may comprise any suitable polymer, typically an ion exchange resin, for example comprising a polymeric anion or cation exchange membrane, or combination thereof. The mobile phase of such a membrane may comprise, and/or is responsible for the primary or preferential transport (during operation of the battery) of at least one mono-, di-, tri-, or higher valent cation and/or mono-, di-, tri-, or higher valent anion, other than protons or hydroxide ions.

Suitable solid cationic exchange polymers include use of one or more of the following polymers: cross-linked halogenated alkylated compound with a polyamine, a cross-linked aromatic polysulfone type polymer with a polyamine, perfluorinated hydrocarbon sulfonate ionomers, sulfonated poly ether ether ketone (sPEEK), sulfonated poly(phthalazinone ether ketone), sulfonated phenolphthalein poly(ether sulfone), sulfonated polyimides, sulfonated polyphosphazene, sulfonated polybenzimidazole, aromatic polymers containing a sulfonic acid group, sulfonated perfluorinated polymer, fluorinated ionomers with sulfonate groups, carboxylate groups, phosphate groups, boronate acid groups, polyaromatic ethers with sulfonate or carboxylate groups, poly(4-vinyl pyridine), poly(2-vinyl pyridine), poly(styrene-b-2-vinylpyridine), poly(vinyl pyrrolidine), poly(1-methyl-4-vinylpyridine), poly[(2,2'-m-phenylene)-5,5'-bibenzimidazole][poly(2,2'-(m-phenylene)-5,5-'-bibenzimidazole], poly(2,5-benzimidazole), polyacrylate, polymethacrylate or combinations thereof. Suitable solid anionic exchange membranes include the use of one or more of the following polymers: polydiaryl dimethyl ammonium, poly(methacaryloxyloxyethyl triethylammonium), poly(diallylammonium), or combinations thereof.

Additionally, substantially non-fluorinated membranes that are modified with sulfonic acid groups (or cation exchanged sulfonate groups) may also be used. Such membranes include those with substantially aromatic backbones, e.g., poly-styrene, polyphenylene, bi-phenyl sulfone (BPSH), or thermoplastics such as polyetherketones or polyethersulfones.

Other examples of ion-exchange membranes comprise Nafion™ (112, 117, HP, XL, NR-212, or U5), Gore Select membranes, Flemion™, and Selemion™.

Battery-separator style porous membranes, may also be used. Because they contain no inherent ionic conduction capability, such membranes are typically impregnated with additives in order to function. These membranes are typically comprised of a mixture of a polymer, and inorganic filler, and open porosity. Suitable polymers include those chemically compatible with the electrolytes of the presently described systems, including high density polyethylene, polypropylene, polyvinylidene difluoride (PVDF), or polytetrafluoroethylene (PTFE). Suitable inorganic fillers include silicon carbide matrix material, titanium dioxide, silicon dioxide, zinc phosphide, and ceria and the structures may be supported internally with a substantially non-ionomeric structure, including mesh structures such as are known for this purpose in the art.

Membranes may also be comprised of polyesters, poly (ether-ketone-ether-ketone-ketone), poly(vinyl chloride), vinyl polymers, substituted vinyl polymers, alone or in combination of any previously described polymer.

Membranes may also comprise reinforcement materials for greater stability. Suitable reinforcement materials include nylon, cotton, polyesters, crystalline silica, crystalline titania, amorphous silica, amorphous titania, rubber, asbestos wood or combination thereof. The volume percent of a reinforcement material may be determined at a given membrane thickness by the following example. The reinforcement material percent is determined from Equation (11):

$$\text{Desired thickness} = \text{starting membrane thickness}/(1-\text{reinforcement vol \%}) \quad (11)$$

For example, the membrane should contain about 33% reinforcement material by volume starting with a membrane of 10 micrometers with a desired thickness of 15 micrometers.

Suitable membranes also comprise continuous membranes. The continuous membranes comprise at least a material in a continuous or discontinuous structure and a filler material that is a continuous or discontinuous structure. Suitable materials in a continuous or discontinuous structure comprises one or more of polyethylene, polypropylene, poly(tetrafluoroethylene), poly(vinyl chloride), or a combination thereof. Suitable filler material in a continuous or discontinuous structure comprises one or more of nonwoven fibers or naturally occurring substances. Suitable nonwoven fibers comprises one or more of nylon, cotton, polyesters, crystalline silica, amorphous silica, amorphous titania, crystalline titania or a combination thereof. Suitable naturally occurring substances comprise one or more of rubber, asbestos, wood or combination thereof. The continuous membrane may also be porous. Suitable porosity is in the range of about 5 to about 75% volume fraction.

Suitable separators may also have a plurality of layers. For instance, a suitable separator comprises a layer capable of ionic conduction and at least one layer capable of selective ion transport. The layer capable of ionic conduction comprises at least one of either the first electrolyte or the second electrolyte imbibed in to the separator. The electrolyte solution, for example potassium chloride (KCl), becomes imbibed into the separator and does not substantially seep out from the polymer matrix. The desired areal resistance range for the imbibed separator is determined by Equation (12):

$$R_{total}[\text{ohm-cm}^2] = K_{membrane} / 10\text{E-}6 \text{ m} + (\text{porosity}_{sep}{}^{\wedge}1.5 * K_{electrolyte})/\text{thickness}_{sep} \quad (12)$$

where R is the resistance, $K_{membrane}$ is the conductivity of the membrane, $K_{electrolyte}$ is the conductivity of the electrolyte, $\text{porosity}_{sep}$ is the porosity of the separator and $\text{thickness}_{sep}$ is the thickness of the separator. Any inert electrolyte, such as NaCl, KCl or the like, is suitable. One of ordinary skill in the art will appreciate suitable inert electrolytes suitable for this purpose. The layer capable of selective ion transport comprises any of the above mentioned solid cationic polymers. Other layers are envisioned within the scope of this invention that may enhance or reduce properties such as conduction, strength, thickness, selectivity, permeability, or the like.

Suitable separators include those separators capable of having a selectivity of at least between about 50 to about 300 for at least one mobile ion over the any present active material. Suitable separators are capable of having a selectivity of at least between about 100 to about 200, and between at least about 50 to about 100 for at least one mobile ion over any present active material.

In either an on-load or off-load condition, there may exist a significant difference in the concentration of active material species in the positive and negative electrolytes in a region of a cell. Despite the presence of the separator, there always exists some finite flux of these species across it due to these concentrations differences since all separators exhibit some permeability. When these species crossover, a loss of energy efficiency occurs since charged species are self-discharging through direct interaction, but also the potential for electrolyte regeneration exists if the battery employs different active material compounds. It is of interest to develop a flow battery chemistry and cell configuration whereby the losses due to diffusive crossover of active materials from either electrolyte to the other do not, in total, exceed 2% of the current in an on-load condition in charge or discharge mode, preferably <("less than") 1%, and most preferably <<("much smaller than") 1% for the reasons provided above.

Suitable separators include those separators where the separator is capable of excluding at least about 98% of at least one of the active materials. Preferably, the separator is capable of excluding at least about 99.0% of at least one of the active materials, and at least about 99.5% of the active materials.

When constructing practical flow battery cells, the electrodes may slightly permeate the separator and result in electrical shorting in a region of a cell. This facilitates the direct exchange of electrons across those shorts, which represents another form of self-discharge leading to current efficiency loss. Flow battery design generally includes a desired combination of separator mechanical properties (i.e., strength), diffusion media properties, cell geometry, and cell mechanical loading. It is of interest to develop a flow battery chemistry and cell configuration whereby the losses due to electrical shorts, in total, exceed 2% of the current in an on-load condition in charge or discharge mode.

Suitable separators are separators which are characterized as having a conductivity of about 0.01 to about 0.06 S/cm for $Li^+$, $Na^+$, and/or $K^+$ and a conductivity of about less than 0.03 S/cm for $Cl^-$, $Br^-$, $I^-$, and/or $OH^-$.

In an on-load condition during charge or discharge in a region of a flow battery cell, ionic current must flow across the separator during the course of the operation. It is desired that most of the ionic current demand be carried by mobile ions provided by supporting species in the electrolyte. However, if the active materials are ionically charged, they may participate in carrying some portion of the ionic current demand, which depends on their transference. Significant transference of active materials occurs during the course of charge or discharge represents yet another form of self-discharge leading to current efficiency losses. It is of interest to develop a flow battery chemistry and cell configuration whereby the transference of active materials from either electrolyte to the other do not, in total, exceed 2% of the current in an on-load condition in charge or discharge mode, preferably <1%, and most preferably <<1% for the reasons provided above.

A portion of the cell geometry may contain an active area. It is desirable for at least a portion of the active area to be comprised of channels. The channels are largely open to the flow of electrolytes and portions of an electrically conductive plate material that electrically connects the electrodes either directly or through diffusion media. Conversely, it is suitable for the active area to be substantially formed of a region that is permeable to the flow of either the first electrolyte or second electrolyte, and whose volume is comprised partially of a high surface area, electrically conducting media.

A suitable flow battery is capable of a cell mechanical loading being able to withstand a mechanical load in the range of about 1 to about 1000 psig. Preferably, the flow battery is capable of withstanding a mechanical load of in the range of about 3 to about 500 psig, and more preferably between about 5 to about 100 psig.

In an on-load condition during charge or discharge in a flow battery cell, there may exist the potential for the current to be consumed in undesirable side reactions. Such side reactions include corrosion of cell materials, decomposition of the active material structure, or decomposition of the electrolyte. This is especially true where significant non-uniformities in concentration, voltage, or current density exist across the cell area. It is of interest to develop a flow battery chemistry and cell configuration whereby the current lost in parasitic reactions does not, in total, exceed 4% of the current in an on-load condition in charge or discharge mode, preferably <2%, and most preferably <1% for the reasons provided above.

Flow batteries are comprised of cells stacked in a bipolar configuration whereby the active materials are fed to either or both the positive and negative electrolyte chambers through common manifolds. Since these electrolytes are ionically conductive, their presence in a common manifold results in positive ionic current being driven from cells towards the positive end of the stack to those towards the negative end. This process will occur in both the positive and negative electrolyte manifolds, and will represent yet another form of self-discharge and current efficiency loss. It is of interest to develop a flow battery chemistry and cell/stack configuration whereby the current losses represented by shunt currents do not, in total, exceed 5% of the current in an on-load condition in charge or discharge mode, preferably <3%, and most preferably <2% for the reasons provided above.

The open circuit potential (OCV) of an electrochemical cell is a relevant operating characteristic of electrochemical energy storage systems. In certain embodiments, the OCV may be comparatively large (e.g. greater than about 1 V). Such comparatively large open circuit potentials are known to enable high cell voltage efficiencies, high AC-AC conversion efficiencies, high energy storage densities, and low system costs. Traditional flow batteries with aqueous electrolytes and soluble active materials may operate with an OCV less than about 1.2 V. An electrochemical cell according to the present disclosure is suitably characterized by an open circuit potential of at least about 1.4 V.

The novel electrolytes of the present invention may provide the open circuit voltages (OCVs) of the flow battery of at least about 0.8 volts, at least about 0.9 V, at least about 1.0 V, at least about 1.1 V, least about 1.2 volts, at least about 1.3 V, at least about 1.4 V, at least about 1.5 V, at least about 1.6 V, at least about 1.7 V, at least about 1.8 V, at least about 1.9 V, or at least about 2 V. As described above, higher open circuit voltages are associated with higher power densities.

The present disclosure presents exemplary cyclic voltammetry data for several metal ligand coordination compound couples under a range of conditions (see Tables 2 and 3). In considering these (or other) sets of half-cell couples, certain embodiments provide that the cells comprise those pairs of metal ligand coordination compounds whose couples provide large open circuit potential, while capable of operating at potentials that are within the potentials associated with the generation of hydrogen and oxygen derived from the electrolysis of water (i.e., so as to operate at potentials where the generation of a hydrogen or oxygen evolution current is minimized or avoided). In certain embodiments, these half-cell couples are chosen to provide large open circuit voltages while operating at or below a half-cell potential of 0 V at the negative electrode and at or above a half-cell potential of 1.23 V at the positive electrode, where the half-cell potentials are with respect to a reversible hydrogen electrode. Through judicious choice of electrode materials which exhibit poor catalytic activity, e.g., an allotrope of carbon or a metal oxide, it is possible to provide systems having large overpotentials, so as to drive the OCV to values higher than the thermodynamic limit of 1.23 V without hydrogen or oxygen evolution. For example, experiments show (and as reflected in Table 3 below) the $Ti^{4+/3+}(cat)_3^{2-/3-}$ and $Al(cit)_2(cat)^{2-/3-}$ pair of couples can exhibit an OCV of 1.73 V using carbon electrodes Systems and methods according to the present disclosure may exhibit a particular current density at a given round trip voltage efficiency. Methods for determining current density at a given round trip voltage efficiency are known to those skilled in the art of electrochemistry and electrochemical energy storage.

To serve as a metric for electrochemical cell performance, a specified current density is generally linked to a measured voltage efficiency. Higher current densities for a given round trip voltage efficiency enable lower cost electrochemical cells and cell stacks. In certain embodiments, it is desired to operate a flow battery with a current density greater than about 50 mA/cm² at $V_{EFF,RT}$ greater than about 50%. In other embodiments, the current density will be greater than about 50 mA/cm² at $V_{EFF,RT}$ greater than about 60%, greater than about 75%, greater than about 85%, greater than about 90%. In other embodiments, the current density will be greater than 100 mA/cm² at $V_{EFF,RT}$ greater than about 50%, greater than about 60%, greater than about 75%, greater than about 85%, greater than about 90% and the like. In other embodiments, the current density will be greater than 200 mA/cm² at $V_{EFF,RT}$ greater than about 50%, greater than about 60%, greater than about 75%, greater than about 85%, greater than about 90%, and above.

Electrolytes that include an organic active material, either in the absence or presence of metal coordination, are considered suitable for one or both half-cells of the disclosed systems and methods. Suitable organic active materials include carbon, aromatic hydrocarbons, including quinones, hydroquinones, viologens, pyridinium, pyridine, acridinium, catechols, other polycyclic aromatic hydrocarbons, and the like. Suitable organic active materials may also include sulfur, including thiol, sulfide, and disulfide moieties. Suitable organic active materials may be soluble in water in concentrations greater than 0.1 M, greater than 0.5 M, greater than 1 M, greater than 1.5 M, greater than 2 M, and above.

The disclosed systems and methods may also be characterized in terms of their half-cell potentials. Both the negative and positive electrode may exhibit a half-cell potential. An electrochemical cell according to the present disclosure may, in some embodiments, have a half-cell potential for the negative electrode less than about 0.5 V vs. RHE, less than about 0.2 V vs. RHE, less than about 0.1 V vs. RHE, less than about 0.0 V vs. RHE, less than about −0.1 V vs. RHE, less than about −0.2 V vs. RHE, less than about −0.3 V vs. RHE, less than about −0.5 V vs. RHE. An electrochemical cell according to the present disclosure may, in some embodiments, have a half-cell potential for the positive electrode greater than about 0.5 V vs. RHE, greater than about 0.7 V vs. RHE, greater than about 0.85 V vs. RHE, greater than about 1.0V vs. RHE, greater than about 1.1V vs. RHE, greater than about 1.2V vs. RHE, greater than about 1.3 V vs. RHE, greater than about 1.4 V vs. RHE and the like.

The disclosed systems and methods may also be characterized in terms of their energy density, as defined above. Flow batteries of the present disclosure may operate with an energy density in excess of about 5 Wh/L, of about 10 Wh/L, excess of about 15 Wh/L, of about 20 Wh/L, excess of about 25 Wh/L, of about 30 Wh/L, excess of about 35 Wh/L, of about 40 Wh/L, or between about 5 Wh/L and about 15 Wh/L, between about 10 Wh/L and about 20 Wh/L, between about 20 Wh/L and about 30 Wh/L, between about 30 and about 40 Wh/L, between about 25 Wh/L and about 45 Wh/L, and above 45 Wh/L.

Example 1—General

The following Examples are provided to illustrate some of the concepts described within this disclosure. While each Example is considered to provide specific individual embodiments of composition, methods of preparation and use, none of the Examples should be considered to limit the more general embodiments described herein.

Example 1.1—Materials

Sodium hexacyanoferrate(II) decahydrate 99%, $Na_4Fe(CN)_6 \cdot 10H_2O$; potassium hexacyanoferrate(II) trihydrate 98+%, $K_4Fe(CN)_6 \cdot 3H_2O$; and potassium hexacyanoferrate (III) ACS 99.0% min, $K_3Fe(CN)_6$ were purchased from Alfa Aesar (Ward Hill, Mass.) and used without additional purification. Potassium hexacyanochromate(III), $K_3[Cr(CN)_6]$ and potassium hexaycyanomanganate(III), $K_3[Mn(CN)_6]$ were purchased from Sigma-Aldrich (St. Louis, Mo.) and used without additional purification.

Disodium titanium(IV) triscatecholate, $Na_2Ti(catecholate)_3$ was synthesized by a modification of a procedure described by Davies, see Davies, J. A.; Dutramez, S. J. Am. Ceram. Soc. 1990, 73. 2570-2572, from titanium(IV) oxysulfate and pyrocatechol. Sodium hydroxide was used in place of ammonium hydroxide to obtain the sodium salt. Sodium potassium titanium(IV) trispyrogallate, $NaKTi(pyrogallate)_3$ was made analogously, first as the ammonium salt, $(NH_4)Ti(pyrogallate)_3$, and subsequently converted to the sodium potassium salt by heating in a mixture of aqueous sodium hydroxide and aqueous potassium hydroxide.

The mixed ligand titanium complexes sodium potassium titanium(IV) biscatecholate monopyrogallate, sodium potassium titanium(IV) biscatecholate monolactate, sodium potassium titanium (IV) biscatecholate monogluconate, sodium potassium titanium(IV) biscatecholate monoascorbate, and sodium potassium titanium(IV) bis catecholate monocitrate were made from a titanium catecholate dimer, $Na_2K_2[TiO(catecholate)]_2$. For the synthesis of the tetrapotassium salt see Borgias, B. A.; Cooper, S. R.; Koh, Y. B.; Raymond, K. N. Inorg. Chem. 1984, 23, 1009-1016. A one-to-one mixture of titanium dimer with the desired chelate (pyrogallol, lactic acid, gluconic acid, ascorbic acid, or citric acid) gave the mixed ligand species. Sodium potassium titanium(IV) monocatecholate monopyrogallate monolactate was made in a similar fashion by addition of both pyrogallol and lactic acid to the catecholate containing dimer. Mixed ligand analogs of the Al, Cr, and Fe compounds may be prepared by similar reaction schemes. The structures of several of the titanium compounds were confirmed by mass spectroscopy (see Table 1).

TABLE 1

Mass spectroscopy for selected compounds

| | Mass (m/z) Calc'd/Obs'd |
|---|---|
| Ti(catecholate)$_3^{2-}$ | 186.0080/186.0 |
| Ti(pyrogallate)$_3^{2-}$ | 210.0038/210.0 |

TABLE 1-continued

Mass spectroscopy for selected compounds

| | Mass (m/z) Calc'd/Obs'd |
|---|---|
| Ti(catecholate)$_2$(pyrogallate)$^{2-}$ | 194.0055/194.0 |
| Ti(catecholate)$_2$(ascorbate)$^{2-}$ | 219.0057/219.0 |
| Ti(catecholate)$_2$(gluconate)$^{2-}$ | 229.0188/229.0 |
| Ti(catecholate)$_2$(lactate)$^{2-}$ | 176.0055/176.0 |

* Mass spectrometry data were obtained on an Agilent 6150B single quadrupole LC/MS in the negative ion mode with electrospray ionization (ESI). Aqueous solution samples of the metal ligand complex were diluted in methanol and introduced to the mass spectrometer ionizer by direct injection using a syringe pump. The reported m/z peaks in each case are for the dianions, z = −2.

Sodium potassium iron(III) triscatecholate, $Na_{1.5}K_{1.5}Fe(catecholate)_3$ was prepared according to the procedure outline by Raymond et. al., see Raymond, K. N.; Isied, S. S., Brown, L. D.; Fronczek, F. R.; Nibert, J. H. J. Am. Chem. Soc. 1976, 98, 1767-1774. The only modification was the use of a mixture of sodium hydroxide and potassium hydroxide as the excess base in place of potassium hydroxide.

Sodium titanium(IV) triscitrate, $Na_4Ti(citrate)_3$, was synthesized by analogy to the method used for sodium titanium (IV) tricatecholate described above except using citric acid in place of catechol. These starting materials were obtained from Alfa Aesar (Ward Hill, Mass.), were of reagent grade or better, and were used as received.

Sodium aluminum(III) biscitrate monocatecholate, $Al(citrate)_2(catecholate)$, was synthesized in analogy to the method used for sodium titanium(IV) tricatecholate described above except using two equivalents of citric acid and one equivalent of catechol to a solution of aluminum (III) sulfate. These starting materials were obtained from Alfa Aesar (Ward Hill, Mass.), were of reagent grade or better, and were used as received.

Example 1.2—Cyclic Voltammetry

Cyclic voltammetry data was recorded using a 760c potentiostat (CH Instruments, Austin, Tex.) with iR correction. Tests were conducted using glassy carbon working electrodes (Bioanalytical Systems, Inc., West Lafayette, Ind.), Ag/AgCl reference electrodes (Bioanalytical Systems, Inc. West Lafayette, Ind.) and platinum wire counter electrodes (Alfa Aesar, Ward Hill, Mass.). Working electrodes were polished according to the supplier's instructions before each experiment. Reference electrodes were calibrated against a "master" Ag/AgCl electrode known to have a potential of +0.210 V vs. NHE as known by those skilled in the art of electrochemistry. Solutions were sparged with argon for at least 5 minutes before each experiment. All experiments were performed at ambient temperatures (17-22° C.). No supporting electrolytes were added unless otherwise specified. All data were collected at a scan rate of 100 mV/s unless otherwise specified. Under these conditions, hydrogen evolution became significant at potentials more negative than −0.80 V vs. RHE and oxygen evolution became significant at potentials more positive than +2.20 V vs. RHE.

Example 1.3—Experimental Procedure for a 5 cm$^2$ Active Area Flow Battery

Cell hardware designed for 5 cm$^2$ active area and modified for acid flow was obtained from Fuel Cell Technologies (Albuquerque, N. Mex.). Carbon felt, nominally 3 mm thick, was obtained from Alfa Aesar (Ward Hill, Mass.). Felts were dip-coated with a suspension of Vulcan XC-72 carbon (Cabot Corp., Boston, Mass.) and NAFION™ (Ion-Power, New Castle, Del.) and air-dried before use. NAFION™ HP, XL, or NR-212 cation exchange membranes were obtained from Ion-Power. Viton™ gaskets were obtained from McMaster Carr (Robinsville, N.J.) and were cut to allow for a 5 cm² active area with ~1 cm² areas left above and below the felts for electrolyte ingress and egress from the positive and negative compartments of the cell. The cell was assembled using gaskets that provided a compression of ~25% of the measured thickness of the felts. The membranes and electrodes were not pretreated before assembly. The electrolyte reservoirs were fashioned from Schedule 80 PVC piping with PVDF tubing and compression fittings. Masterflex™ L/S peristaltic pumps (Cole Parmer, Vernon Hills, Ill.) were used with Tygon™ tubing. Electrolytes were sparged with UHP argon through an oil-filled bubbler outlet before electrochemical testing. An Arbin Instruments BT2000 (College Station, Tex.) was used to test the electrochemical performance, and a Hioki 3561 Battery HiTESTER (Cranbury, N.J.) was used to measure the AC resistance across the cell.

In a typical experiment, 50 mL each of electrolyte containing active material for the positive and negative electrode were loaded into separate reservoirs and sparged with argon for 20 minutes while circulating the electrolytes through the cell. The electrolytes were charged to 40% SOC (calculated from the concentrations of the active materials and the volumes of the electrolyte), the iV response of the cell was obtained, and then the electrolytes were cycled between 40 and 60% SOC. An analog output from the Hioki battery tester was recorded to monitor changes in the membrane and contact resistances.

Example 2

Figure 2:
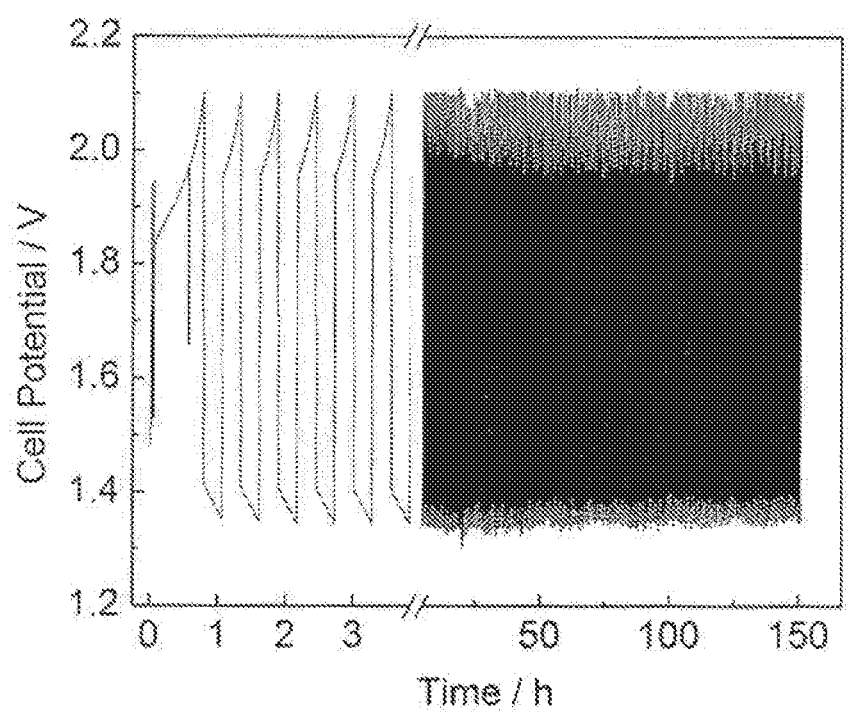
FIG. 2 provides exemplary stability performance data obtained during 250 charge/discharge cycles for a 5 cm$^2$ system based on $Ti^{4+/3+}(cat)_3^{2-/3-}$ and $Fe^{3+/2+}(CN)_6^{3-/4-}$, as described in Example 2.

A redox flow battery cell was assembled according to the methods described in Example 1.3 using titanium triscatecholate ($Ti^{4+/3+}(cat)_3^{2-/3-}$) and ferri/ferro-cyanide ($Fe^{3+/2+}(CN)_6^{3-/4-}$) metal ligand coordination compounds as active materials for the negative and positive electrolytes, respectively. The active materials were prepared at concentrations of 0.5 M in 0.5 M pH 11 $Na_2SO_4$ supporting electrolyte (negolyte) or no supporting posolyte (posolyte) and were flowed at 100 mL/min through the flow battery cell assembled using 5 cm² carbon felt electrodes and a NAFION™ cation selective membrane (50 µm thick) in Na form. The cell was initially charged from 0 to 50% state of charge before several charge/discharge cycles was collected by sweeping the cell current from open circuit to ~150 mA/cm² and monitoring the resulting cell potential, FIG. 2. At open circuit, a cell potential of 1.63 V was observed as expected for equilibrium cell potential at 50% SOC based on the externally measured $E_{1/2}$ values for $Ti^{4+/3+}(cat)_3^{2-/3-}$ and $Fe^{3+/2+}(CN)_6^{3-/4-}$. Charge/discharge cycling revealed well behaved, reproducible voltage/current vs. time traces, demonstrating promising durability, FIG. 2. An RT voltage efficiency of 69% was measured for this system at 150 mA/cm². Typical resistances measured by the Hioki Battery Tester for the membrane and contact resistance component of cells built with NR212, XL, and HP membranes were 0.77, 0.60, and 0.5 .OMEGA.cm², respectively.

Figure 3:
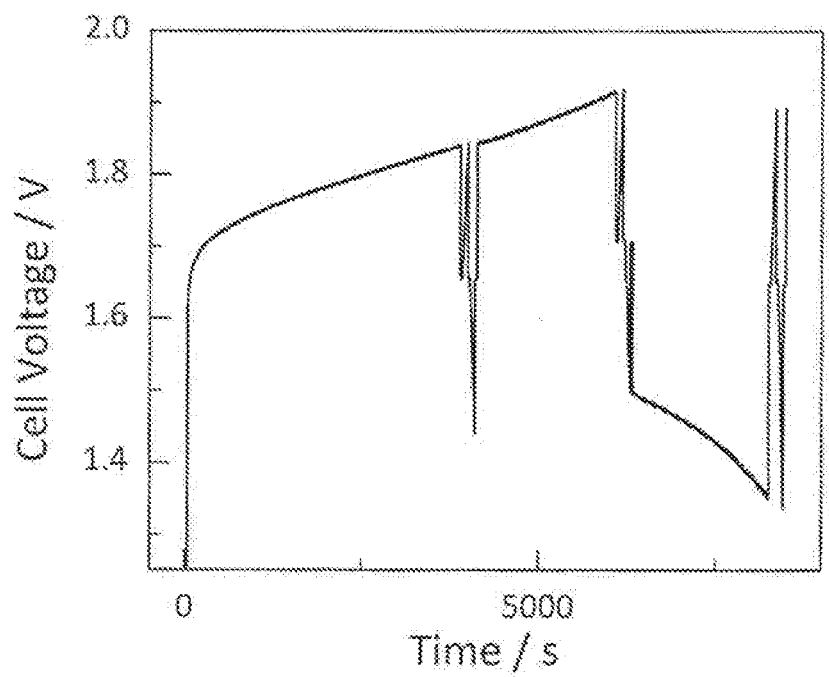
FIG. 3 provides a charge/discharge trace for an exemplary flow battery according to the present invention as described in Example 2. This example contains $Ti^{4+/3+}(cat)_3^{2-/3-}$ and $Fe^{3+/2+}(CN)_6^{3-/4-}$ as first and second electrolytes, respectively. The battery was charged from 0% SOC to 60% SOC and then discharged to 40% SOC at a current density of 200 mA/cm$^2$ and a RT Voltage efficiency of ~76%.

FIG. 3 displays the charge/discharge characteristics for a flow battery of the present invention wherein the negative and positive active materials comprise $Ti^{4+/3+}(cat)_3^{2-/3-}$ and $Fe^{3+/2+}(CN)_6^{3-/4-}$, respectively. The cell potential increases as the battery is charged and decreases as the battery is discharged.

Example 3

Figure 4:
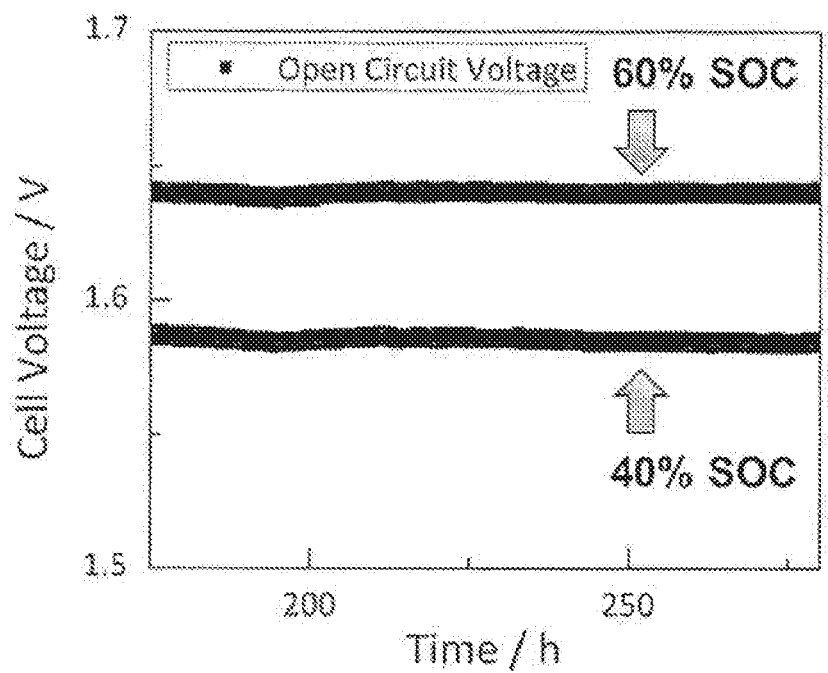
FIG. 4 provides current efficiency data obtained for a system based on $Ti^{4+/3+}(cat)_3^{2-/3-}$ and $Fe^{3+/2+}(CN)_6^{3-/4-}$, as described in Example 3.

A redox flow battery cell was assembled according to the methods described in Example 1.3 using titanium triscatecholate ($Ti^{4+/3+}(cat)_3^{2-/3-}$) and ferri/ferro-cyanide ($Fe^{3+/2+}(CN)_6^{3-/4-}$) metal ligand coordination compounds as active materials for the negative and positive electrolytes, respectively. In a typical cell, stable voltages were observed upon repeatedly charging to 60% SOC and discharging to 40% SOC (see FIG. 4) when the discharge energy for each cycle was 99.8% of the charge energy, indicative of 99.8% roundtrip current efficiency. This was achieved by using a constant current density (e.g., 150 mA/cm²) for both charge and discharge but with a discharge time that was slightly shorter than (i.e., 99.8% of) the charge time. Under these conditions, the open circuit voltages at 40 and 60% SOC were stable for extended periods of time.

Crossover flux data were obtained by measuring the concentrations of Fe and Ti in each electrolyte at the beginning and end of a suitably lengthy battery test, typically one to two weeks in duration for a membrane area of 7 cm². The concentrations were determined by Inductively Coupled Plasma-Mass Spectrometry (ICP-MS) experiments performed by Evans Analytical Group, Syracuse, N.Y. The moles of Fe in the Ti-containing electrolyte before the test were subtracted from the number of moles in the same electrolyte at the end of the test. This was converted to a flux by dividing the moles by the membrane area and the test duration.

Typical fluxes for boiled DuPont Nafion™ NR212 (50 µm thick) were $5.0 \times 10^{-8}$ mol cm$^{-2}$ day$^{-1}$ for ferri/ferrocyanide and $6.5 \times 10^{-8}$ mol cm$^{-2}$ day$^{-1}$ for titanium triscatecholate. For unboiled DuPont Nafion™ HP (20 µm thick), the measured fluxes were $1.1 \times 10^{-5}$ and $3.3 \times 10^{-6}$ mol cm$^{-2}$ day$^{-1}$ for the above iron and titanium complexes, respectively. It should be noted that these fluxes are substantially lower than 1% of the total current (and thus the total moles of ions passed across the membrane) during this time. For example, in the NR212 test above, $6.4 \times 10^{-2}$ mol of total ions were passed over 6.8 days of operation at 100 mA/cm², approximately 6 orders of magnitude larger than the amount of active material ion crossover.

Example 4

Figure 5:
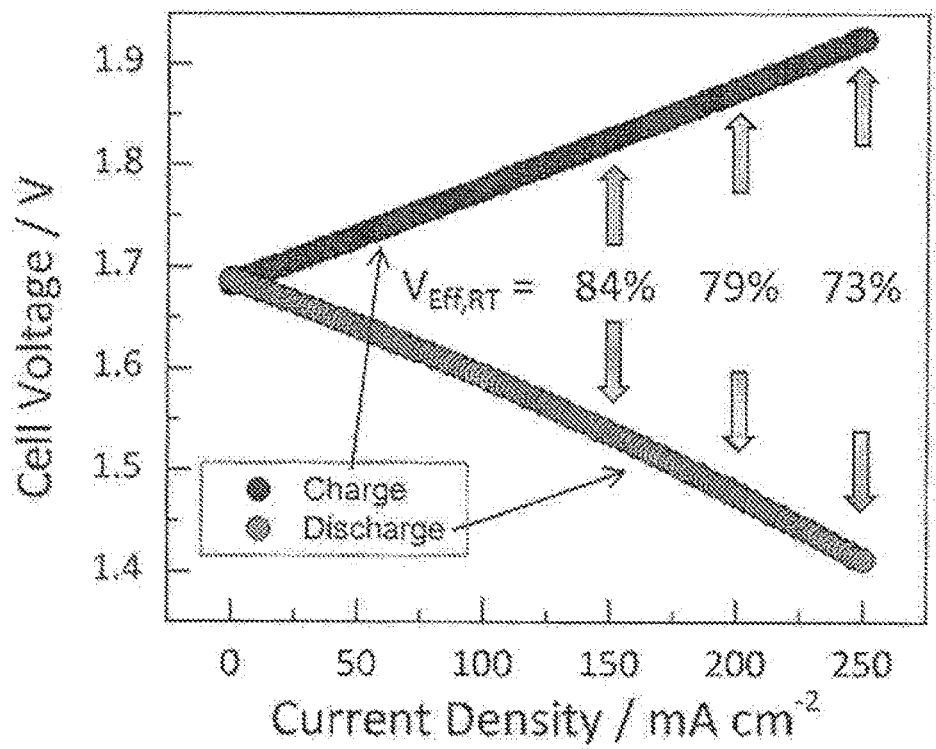
FIG. 5 provides voltage efficiency data, as a function of current density, for a system based on $Ti^{4+/3+}(cat)_2(pyrogallate)^{2-/3-}$ and $Fe^{3+/2+}(CN)_6^{3-/4-}$, as described in Example 4.

A redox flow battery cell was assembled according to the general methods described in Example 1.3, again using titanium bis-catecholate mono-pyrogallate ($Ti^{4+/3+}(cat)_2(gal)^{2-/3-}$) and ferri/ferro-cyanide ($Fe^{3+/2+}(CN)_6^{3-/4-}$) metal ligand coordination compounds as active materials for the negative and positive electrolytes, respectively. In this example the carbon felt electrodes were replaced with TORAY carbon paper electrodes that were catalyzed with Vulcan carbon and NAFION™ in a manner similar to that of Example 2. Additionally, flow fields of the "interdigitated" type were employed. The active material solution concentrations were increased to 1.5 M and the cell performance was evaluated by monitoring the cell potential on both charge and discharge cycles as a function of current density. As can be seen in FIG. 5, the cell maintains round trip voltage efficiencies of 84%, 79%, and 73% at current densities of 150, 200, and 250 mA/cm², respectively. In this configuration the flow battery active materials exhibited an energy density of 32.79 Wh/L.

Figure 6:
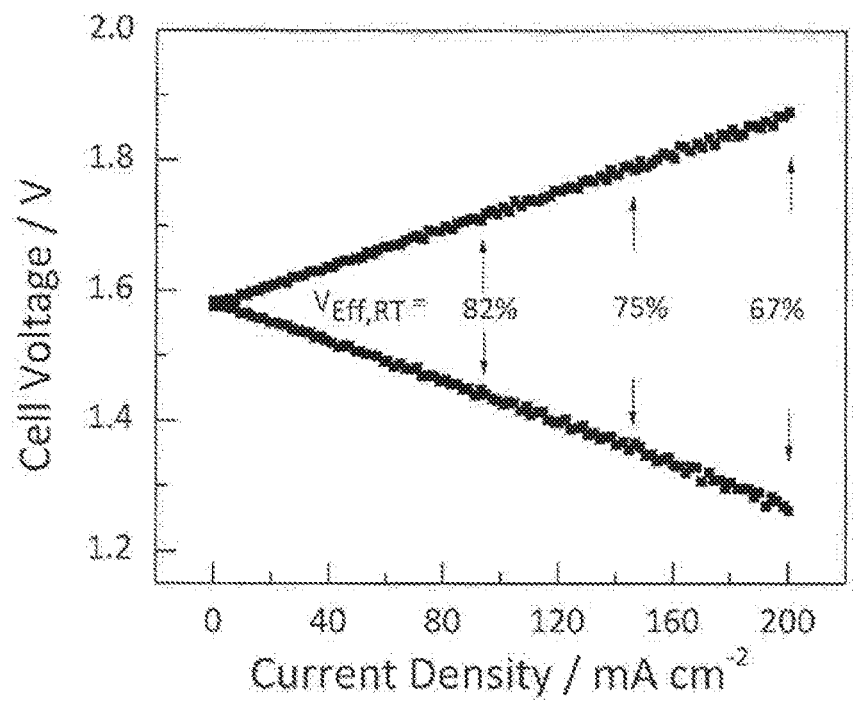
FIG. 6 provides voltage efficiency data, as a function of current density, for a system based on $Ti^{4+/3+}(cat)_3^{2-/3-}$ and $Fe^{3+/2+}(CN)_6^{3-/4-}$, as described in Example 4.
Figure 7:
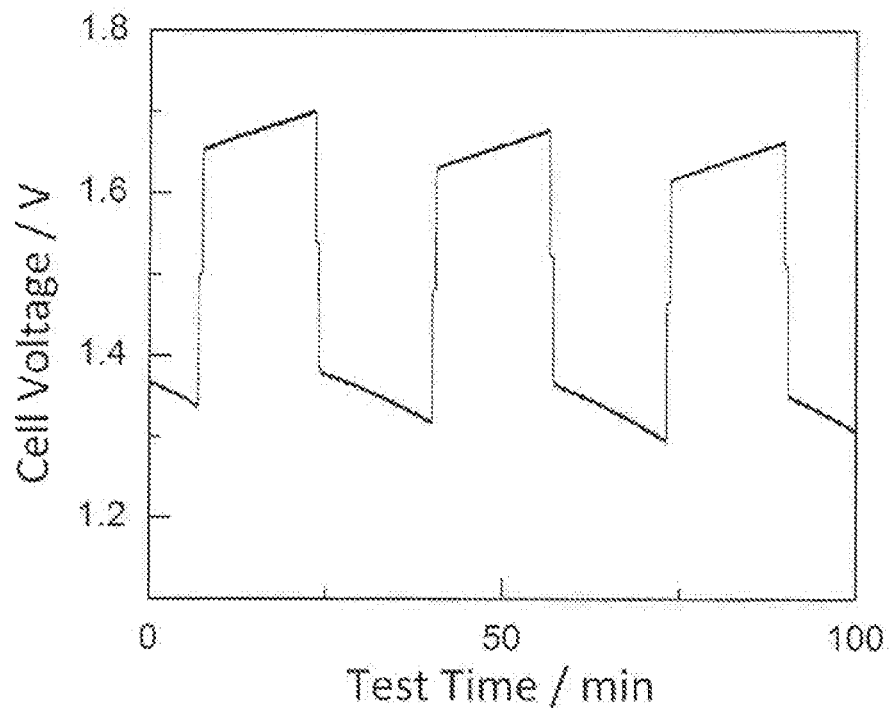
FIG. 7 provides a charge/discharge trace for a flow battery of the present invention. This example contains $Fe^{3+/2+}(cat)_3^{3-/4-}$ and $Fe^{3+/2+}(CN)_6^{3-/4-}$ as first and second electrolytes, respectively. The battery was charged from 0% SOC to 60% SOC and then discharged to 40% SOC at a current density of 100 mA/cm$^2$ and a RT voltage efficiency of ca. 82%.

The results of analogous experiments using $Ti^{4+/3+}(cat)_3^{2-/3-}$ and $Fe^{3+/2+}(CN)_6^{3-/4-}$ are shown in FIG. 6.

Example 5—Cyclic Voltammetry Data

The following experiments provide information as to the nature of the half-cell performance for the indicated materials. As described above, certain embodiments of the present invention include those flow batteries comprising these, or analogous, materials which would provide full cell performance reflective of the reported half-cell performance, and such embodiments are considered within the scope of the present invention.

use of catecholate-like ligands over a range of low and negative operating potentials, under conditions described above, showing the good electrochemical reversibility of these systems under these conditions.

Examples 5.4 through 5.10

Figure 11:
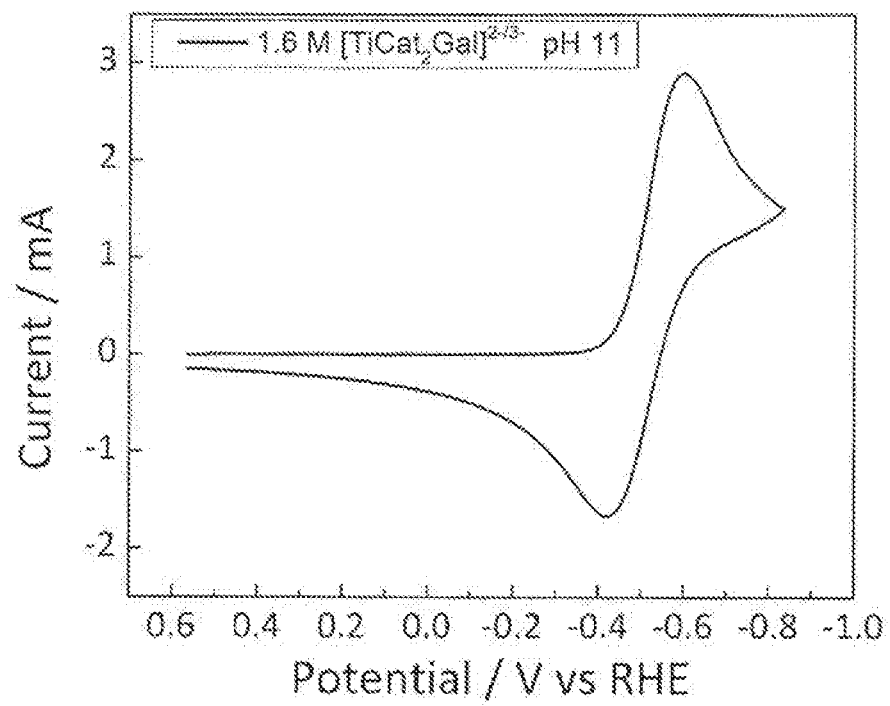
FIG. 11 provides a CV trace for titanium bis-catecholate mono-pyrogallate over a range of operating potentials. The data were generated using solutions of 1.6 M $NaK[Ti(catecholate)_2(pyrogallate)]$ at a pH of 11, recorded at a glassy carbon electrode.
Figure 12:
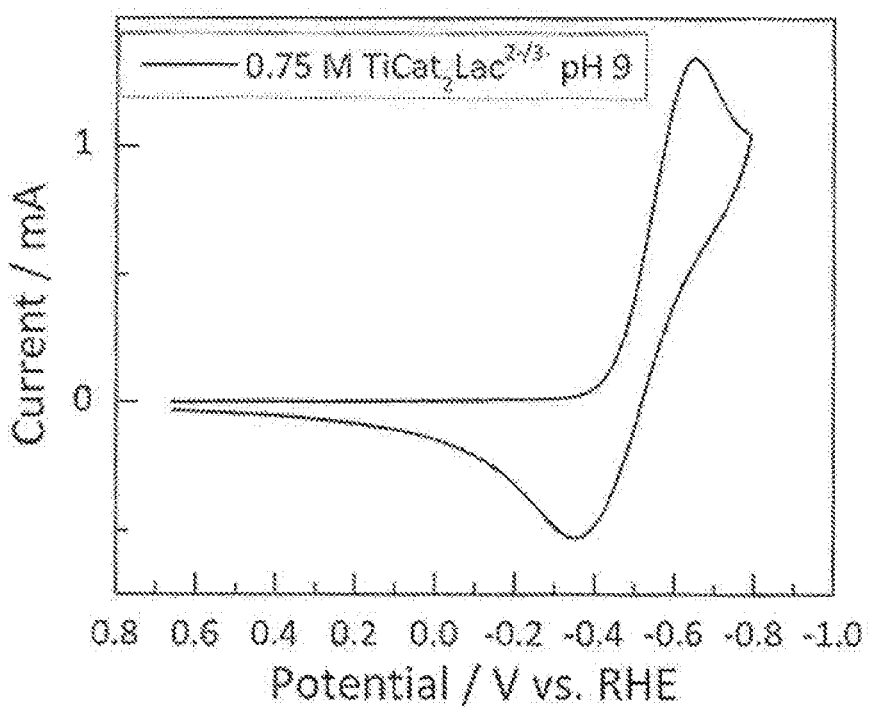
FIG. 12 provides a CV trace for titanium bis-catecholate monolactate over a range of operating potentials. The data were generated using solutions of 0.75 M $NaK[Ti(catecholate)_2(lactate)]$ at a pH of 9, recorded at a glassy carbon electrode.
Figure 13:
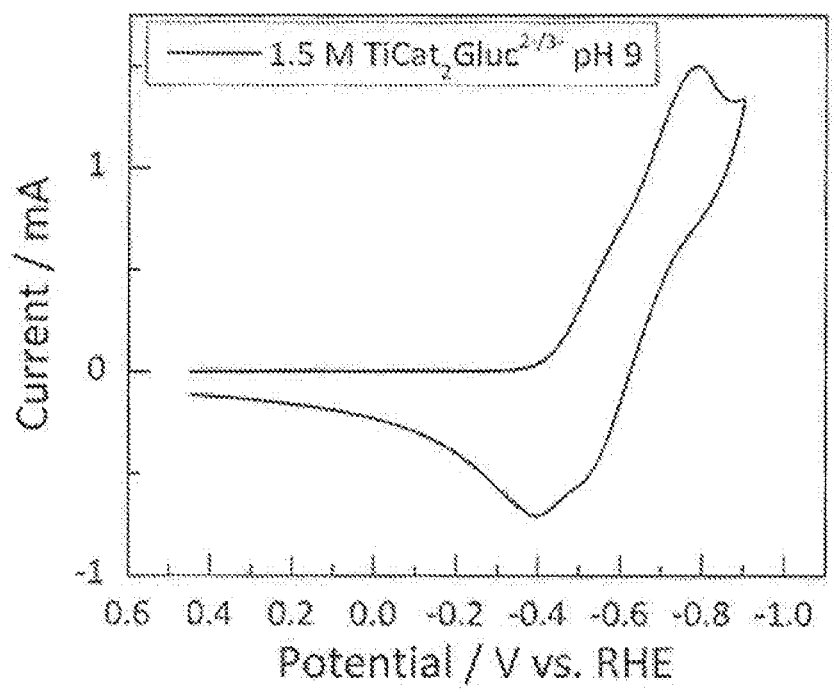
FIG. 13 provides a CV trace for titanium bis-catecholate mono-gluconate over a range of operating potentials. The data were generated using solutions of 1.5 M $NaK[Ti(catecholate)_2(gluconate)]$ at a pH of 9, recorded at a glassy carbon electrode.
Figure 14:
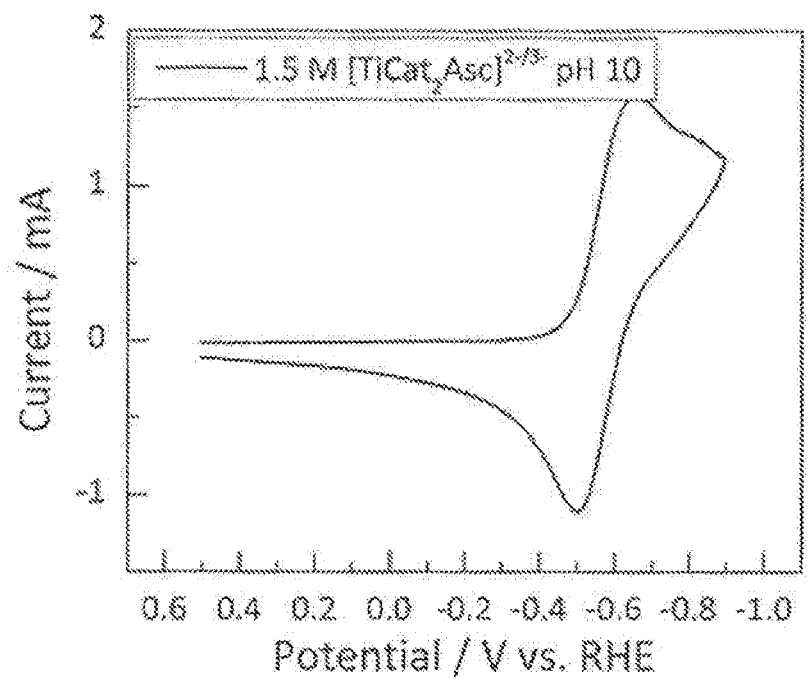
FIG. 14 provides a CV trace for titanium bis-catecholate mono-ascorbate over a range of operating potentials. The data were generated using solutions of 1.5 M $NaK[Ti(catecholate)_2(ascorbate)]$ at a pH of 10, recorded at a glassy carbon electrode.
Figure 15:
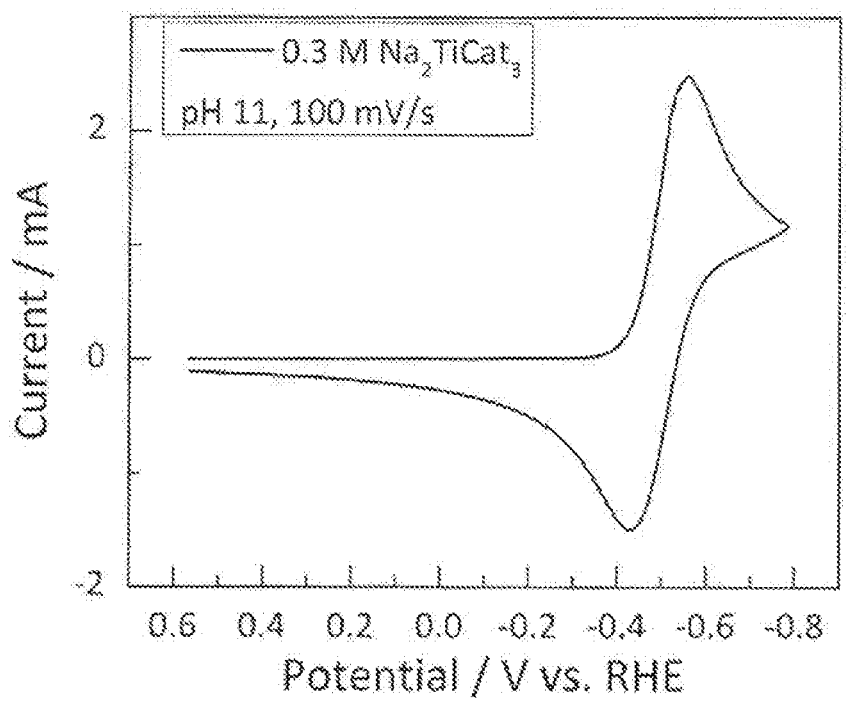
FIG. 15 provides a CV trace for titanium tris-catecholate over a range of operating potentials. The data were generated using solutions of 1.5 M $Na_2[Ti(catecholate)_3]$ at a pH of 11, recorded at a glassy carbon electrode.
Figure 16:
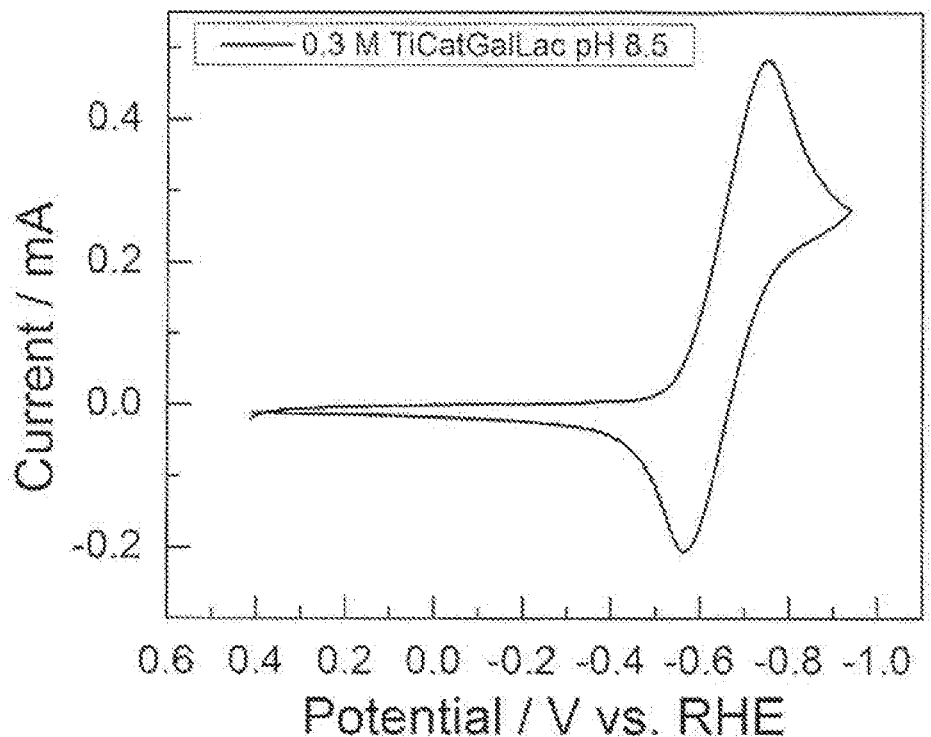
FIG. 16 provides a CV trace for titanium mono-catecholate mono-pyrogallate mono-lactate over a range of operating potentials. The data were generated using solutions of 1.5 M $NaK[Ti(catecholate)(pyrogallate)(lactate)]$ at a pH of 8.5, recorded at a glassy carbon electrode.
Figure 17:
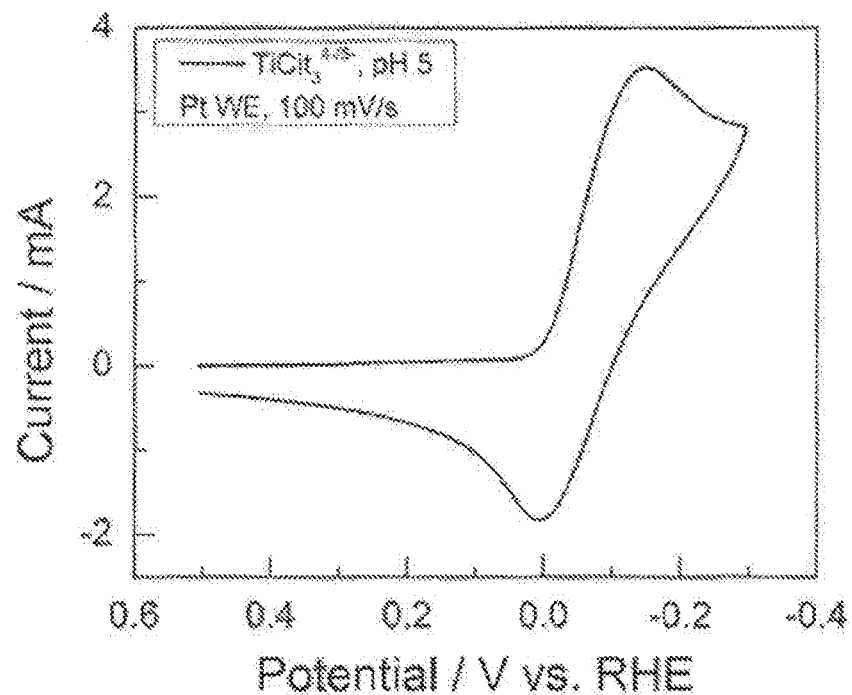
FIG. 17 provides a CV trace for titanium tris-citrate over a range of operating potentials. The data were generated using solutions of 0.5 M $Na_4[Ti(citrate)_3]$ at a pH of 5, recorded at a glassy carbon electrode.

FIG. 11 (NaK[Ti(catecholate)$_2$(pyrogallate)]), FIG. 12 (NaK[Ti(catecholate)$_2$(lactate)]), FIG. 13 (NaK[Ti(catecholate)$_2$(gluconate)]), FIG. 14 (NaK[Ti(catecholate)$_2$(ascorbate)]), FIG. 15 (Na$_2$[Ti(catecholate)$_3$]), FIG. 16 (NaK[Ti(catecholate)(pyrogallate)(lactate)]), and FIG. 17 (Na$_4$[Ti(citrate)$_3$]) illustrate the CV curves resulting from the use of several mixed ligand or tris-citrate systems over a range of low and negative operating potentials, under

TABLE 2

Exemplary electrochemical couples described herein

| Couple | $E_{1/2}$, V vs. RHE | pH | FIG. | Solubility (Molar), 25° C. | Charge Density (Ah/L) |
|---|---|---|---|---|---|
| Al(citrate)$_2$(catecholate)$^{2-/3-}$ | 1.25 | 11.5 | 8 | 0.5 | 13.4 |
| Fe(catecholate)$^{2-/3-}$ | −0.50 | 11 | 10 | 1.5 | 40.2 |
| Ti(catecholate)$^{2-/3-}$ | −0.45 | 11 | 15 | 1.0 | 26.8 |
| Ti(pyrogallate)$^{2-/3-}$ | −0.55 | 9.8 | 9 | 1.6 | 42.9 |
| Ti(catecholate)$_2$(pyrogallate)$^{2-/3-}$ | −0.50 | 11 | 11 | 1.5 | 40.2 |
| Ti(catecholate)$_2$(ascorbate)$^{2-/3-}$ | −0.55 | 10 | 14 | 1.5 | 40.2 |
| Ti(catecholate)$_2$(gluconate)$^{2-/3-}$ | −0.60 | 9 | 13 | 1.5 | 40.2 |
| Ti(catecholate)$_2$(lactate)$^{2-/3-}$ | −0.49 | 9 | 12 | 1.5 | 40.2 |
| Ti(catecholate)(pyrogallate)(lactate)$^{2-/3-}$ | −0.70 | 8.5 | 16 | 1.5 | 40.2 |
| Ti(citrate)$_3^{2-/3-}$ | −0.04 | 5 | 17 | 2.0 | 53.6 |
| Fe(CN)$_6^{3-/4-}$ | 1.18 | 11 | 18 | 1.5 | 40.2 |
| Cr(CN)$_6^{3-/4-}$ | −0.60 | 9 | 19 | 1.5 | 40.2 |
| Mn(CN)$_6^{3-/4-}$ | −0.60 | 9 | 20 | 1.5 | 40.2 |

TABLE 3

Calculated OCVs and theoretical energy density (Wh/L) for various electrolyte couple pairs calculated from data in Table 2

| | Fe(CN)$_6^{3-/4-}$ | | Al(cit)$_2$(cat)$^{2-/3-}$ | |
|---|---|---|---|---|
| Couple | OCV (V) | Energy Density (Wh/L) | OCV (V) | Energy Density (Wh/L) |
| Mn(CN)$_6^{3-/4-}$ | 1.78 | 35.8 | 1.85 | 12.4 |
| Fe(catecholate)$^{2-/3-}$ | 1.68 | 33.8 | 1.75 | 11.7 |
| Ti(catecholate)$^{2-/3-}$ | 1.63 | 21.8 | 1.70 | 11.4 |
| Ti(pyrogallate)$^{2-/3-}$ | 1.73 | 34.8 | 1.80 | 12.1 |
| Ti(catecholate)$_2$(pyrogallate)$^{2-/3-}$ | 1.68 | 33.8 | 1.75 | 11.7 |
| Ti(catecholate)$_2$(ascorbate)$^{2-/3-}$ | 1.73 | 34.8 | 1.80 | 12.1 |
| Ti(catecholate)$_2$(gluconate)$^{2-/3-}$ | 1.78 | 35.8 | 1.85 | 12.4 |
| Ti(catecholate)$_2$(lactate)$^{2-/3-}$ | 1.67 | 33.6 | 1.74 | 11.7 |
| Ti(catecholate)(pyrogallate)(lactate)$^{2-/3-}$ | 1.73 | 34.8 | 1.80 | 12.1 |
| Ti(citrate)$_3^{2-/3-}$ | 1.22 | 24.5 | 1.29 | 8.6 |

Example 5.1

Figure 8:
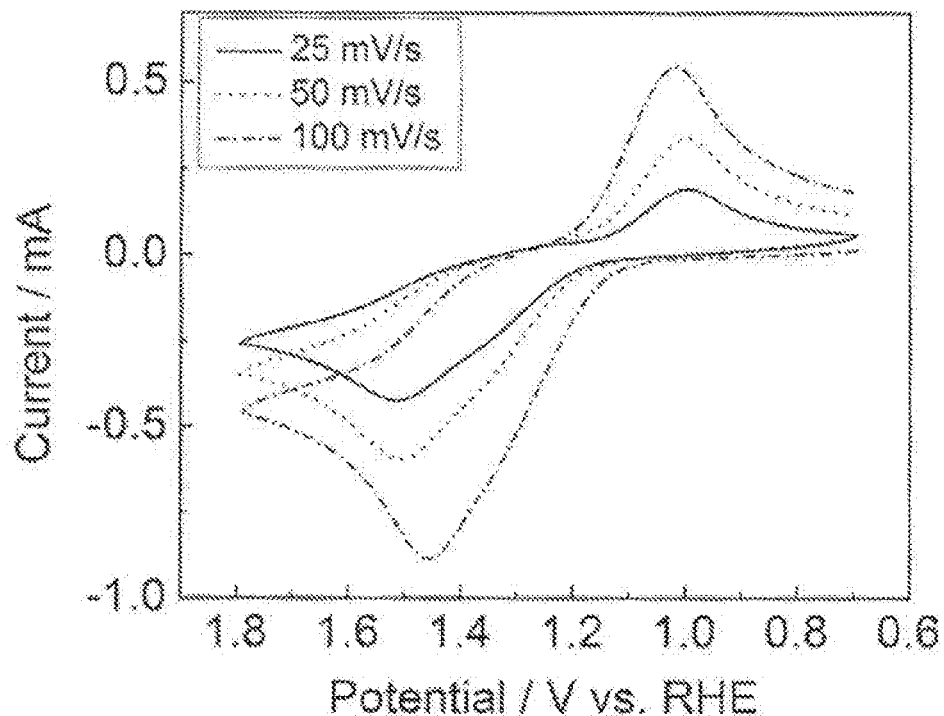
FIG. 8 provides cyclic voltammogram, CV traces for $Al(cit)^2(cat)^{2-/3-}$ in pH 11.5 $Na_2SO_4$ electrolyte recorded at a glassy carbon electrode.

Using an Al(cit)$_2$(cat)$^{2-/3-}$ couple ($E_{1/2}$=~1.25 V vs. RHE) as a demonstrative case, a high potential was observed with well-behaved electrochemical signatures at glassy carbon electrodes, FIG. 8. When coupled with the $Ti^{4+}(cat)_3^{2-}$ complex described above these pairs may give aqueous battery pairs with OCVs of ~1.7-1.9 V.

Examples 5.2 and 5.3

Figure 9:
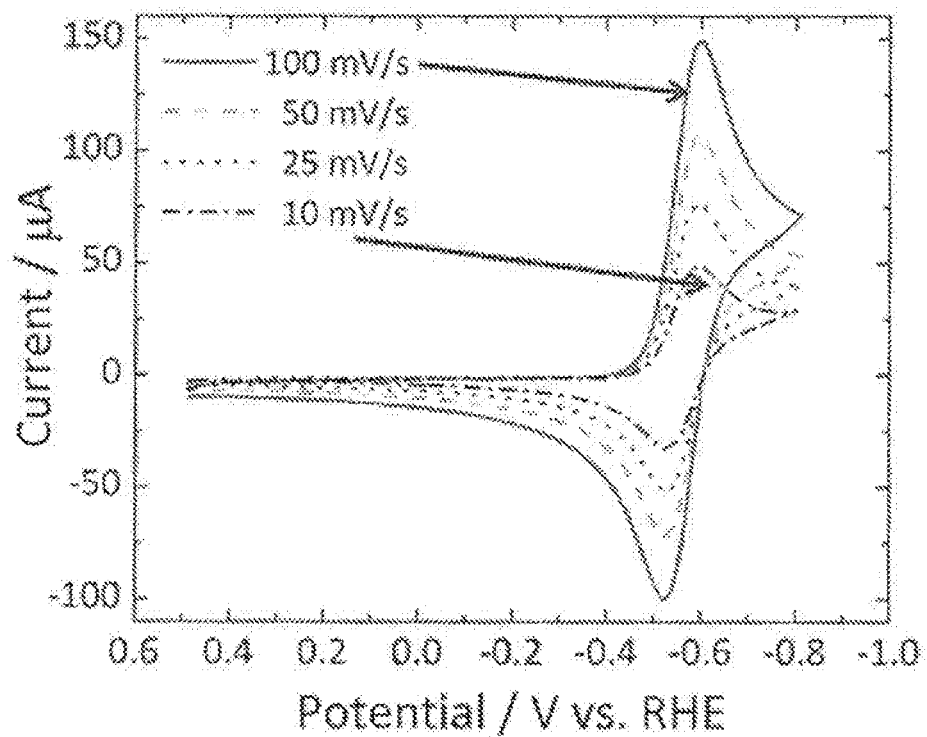
FIG. 9 provides CV traces for titanium tris-pyrogallate over a range of operating potentials. The data were generated using solutions of 75 mM $NaK[Ti(pyrogallate)_3]$ at a pH of 9.8 and 1 M $Na_2SO_4$, recorded at a glassy carbon electrode.
Figure 10:
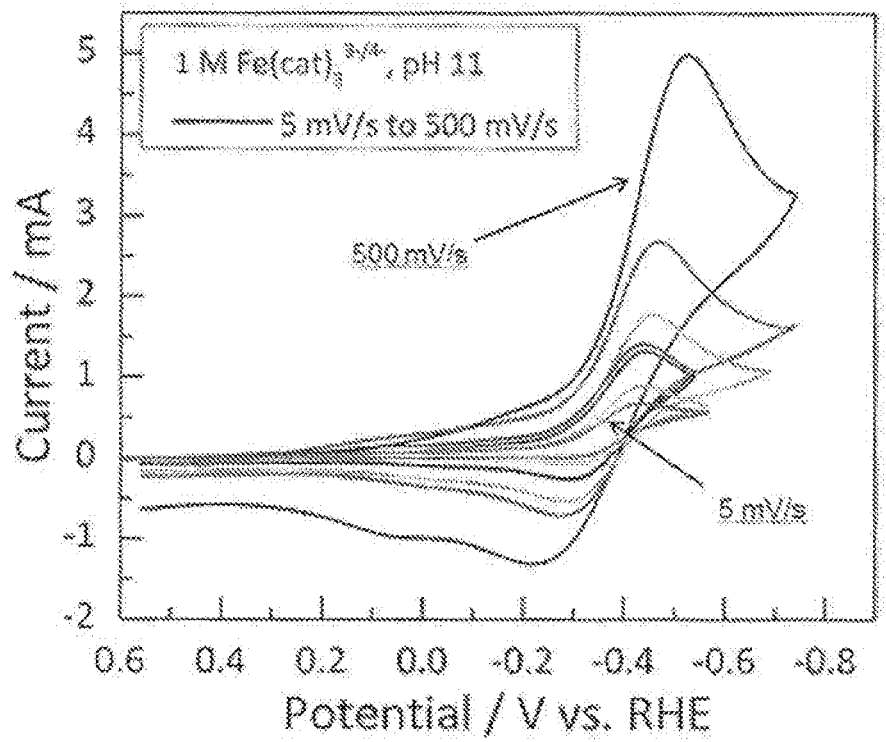
FIG. 10 provides CV traces for iron tris-catecholate over a range of operating potentials. The data were generated using solutions of 1M $NaK[Fe(catecholate)_3]$ at a pH of 11, and 3 M Na/KCl, recorded at a glassy carbon electrode.

FIG. 9 (for titanium tris-pyrogallate) and FIG. 10 (for iron tris-catecholate) illustrate the CV curves resulting from the conditions described above, showing the good electrochemical reversibility of these systems under these conditions.

Example 5.11: Ferrocyanide Samples

Solid Na$_4$Fe(CN)$_6$·10H$_2$O (33.89 g, 0.070 mol) and K$_4$Fe(CN)$_6$·3H$_2$O (29.57 g, 0.070 mol) were stirred in 80 mL deionized water. To dissolve the solids, sufficient water was then slowly added to provide a sample containing ca. 1.5 M of Fe(CN)$_6^{4-}$. This solubility was unexpected given that the solubilities of Na$_4$Fe(CN)$_6$·10H$_2$O and K$_4$Fe(CN)$_6$·3H$_2$O are each known in the art to be less than 0.7 M at the same ambient temperatures.

Figure 18:
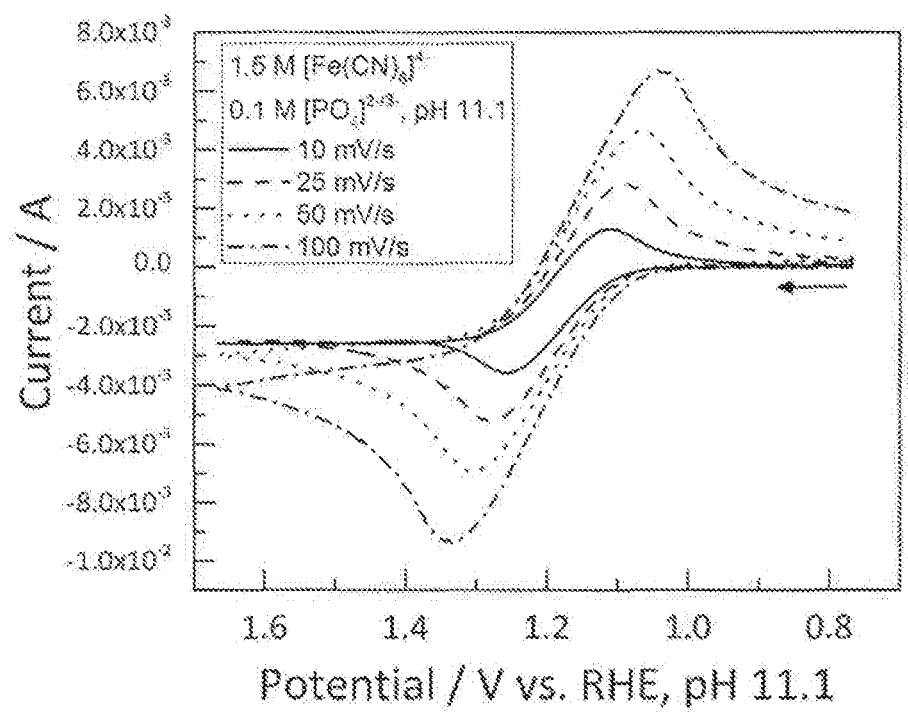
FIG. 18 provides a CV trace from a solution of 1.5 M $[Fe(CN)_6]^{4-}$ obtained at a glassy carbon disk working electrode at several scan rates using 0.1 M sodium potassium hydrogen phosphate as the supporting electrolyte, as described in Example 5.11. The ratio of $Na^+/K^+$ counterions in this example was ca. 1:1.

The 1.5 M [Fe(CN)$_6$]$^{4-}$ solution was interrogated by cyclic voltammetry, using a glassy carbon working electrode. FIG. 18. In these experiments, sufficient solid sodium potassium hydrogen phosphate, NaOH, and KOH was added to the 1.4 M [Fe(CN)$_6$]$^{4-}$ solution to yield a working solution having a pH of 11.1 (ratio N$^+$/K$^+$ about.1) and containing 1.4 M [Fe(CN)$_6$]$^{4-}$ and 0.1 M phosphate.

Examples 5.12 and 5.13

Figure 19:
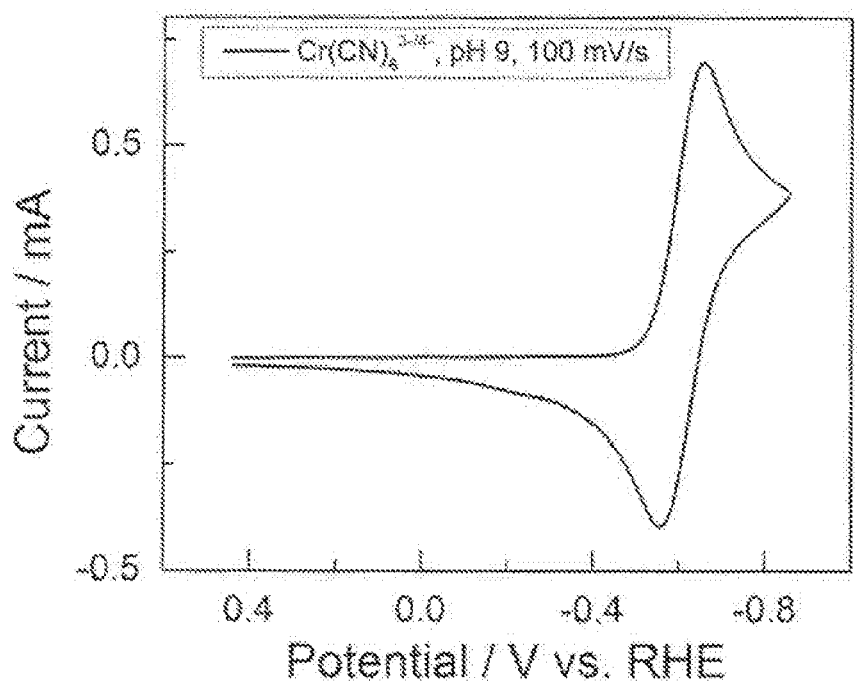
FIG. 19 provides a CV trace for chromium hexacyanide over a range of operating potentials. The data were generated using solutions of 0.05 M $K_3[Cr(CN)_6]$ at a pH of 9, recorded at a glassy carbon electrode.
Figure 20:
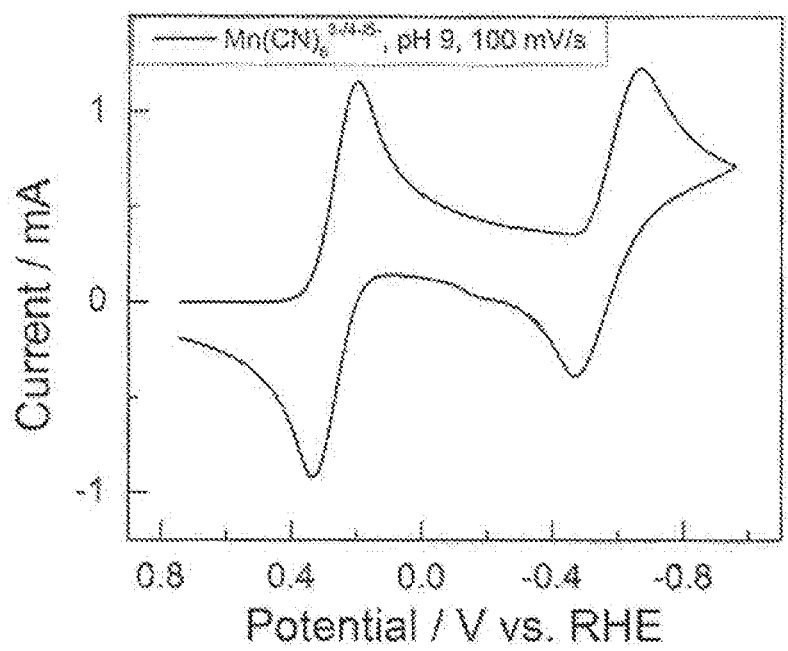
FIG. 20 provides a CV trace for manganese hexacyanide over a range of operating potentials. The data were generated using solutions of 0.1 M $K_3[Mn(CN)_6]$ at a pH of 9, recorded at a glassy carbon electrode.

FIG. 19 (K$_3$[Cr(CN)$_6$]) and FIG. 20 (K$_3$[Mn(CN)$_6$]) illustrate the CV curves resulting from the use of two other hexacyanide systems over a range of low and negative operating potentials, under conditions described above, showing the good electrochemical reversibility of these systems under these conditions.

Many of the embodiments thus far have been described in terms of flow batteries in which at least one metal ligand coordination compounds is described by the formula M(L1)$_{3-x-y}$(L2)$_x$(L3)$_y{}^m$. It should be appreciated, however, that other embodiments include those where the hexacyanide compounds described herein may provide the basis of both of the positive and negative electrolytes. From FIG. 20, for example, it should be apparent that the [Mn(CN)$_6$]$^{3-/4-}$ and [Mn(CN)$_6$]$^{4-/5-}$ couples, in addition to providing the basis of either positive or negative electrolytes, in combination with other complementary electrolytes described herein as M(L1)$_{3-x-y}$(L2)$_x$(L3)$_y{}^m$, may also provide the basis for both the positive and negative electrolytes in a flow battery system. Similarly, independent embodiments also include those where the positive electrolyte comprises [Fe(CN)$_6$]$^{3-/4-}$ and the negative electrolyte comprises [Cr(CN)$_6$]$^{3-/4-}$ or [Mn(CN)$_6$]$^{3-/4-}$.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety.

What is claimed is the following:

1. A composition comprising:
   a titanium complex containing at least one unsubstituted catecholate ligand and at least one substituted catecholate, wherein at least one of the substituted catecholate ligands is a sulfonated catecholate ligand; and sodium and potassium counterions.

2. The composition of claim 1, wherein the titanium complex contains a hydroxycatecholate ligand.

3. The composition of claim 1, wherein the titanium complex contains two unsubstituted catecholate ligands and the one sulfonated catecholate ligand.

4. The composition of claim 1, wherein the titanium complex contains one unsubstituted catecholate ligand, one sulfonated catecholate ligand, and at least one ligand selected from the group consisting of, ascorbate, citrate, glycolate, a polyol, gluconate, glycinate, a hydroxyalkanoate, acetate, formate, benzoate, malate, maleate, phthalate, sarcosinate, salicylate, oxalate, a urea, a polyamine, an aminophenolate, acetylacetonate, and lactate.

5. The composition of claim 1, wherein the sodium and potassium counterions are present in substantially equal molar amounts.

6. An aqueous solution comprising the composition of claim 1.

7. The aqueous solution of claim 6, wherein the titanium complex has a concentration of at least about 0.5 M in the aqueous solution.

8. The aqueous solution of claim 6, wherein the titanium complex contains a hydroxycatecholate ligand.

9. The aqueous solution of claim 6, wherein the titanium complex contains two unsubstituted catecholate ligands and one sulfonated catecholate ligand.

10. The aqueous solution of claim 6, wherein the titanium complex contains one unsubstituted catecholate ligand, one sulfonated catecholate ligand, and at least-one ligand selected from the group consisting of ascorbate, citrate, glycolate, a polyol, gluconate, glycinate, a hydroxyalkanoate, acetate, formate, benzoate, malate, maleate, phthalate, sarcosinate, salicylate, oxalate, a urea, a polyamine, an aminophenolate, acetylacetonate, and lactate.

11. The aqueous solution of claim 6, wherein substantially equal molar quantities of the sodium and potassium counterions are present.

12. A flow battery comprising:
   a first half-cell containing a first electrolyte solution; and
   a second half-cell containing a second electrolyte solution;
   wherein at least one of the first electrolyte solution and the second electrolyte solution comprises the aqueous solution of claim 6.

* * * * *